(12) United States Patent
Rorabaugh et al.

(10) Patent No.: US 8,989,848 B2
(45) Date of Patent: Mar. 24, 2015

(54) APPARATUS AND METHOD FOR NON-INVASIVELY DETECTING DISEASES THAT AFFECT STRUCTURAL PROPERTIES IN BIOLOGICAL TISSUES

(75) Inventors: Dale A. Rorabaugh, Healdsburg, CA (US); Neil M. Davis, Temecula, CA (US); Vincent F. Brancaccio, Eugene, OR (US); Paul Williams, La Jolla, CA (US)

(73) Assignee: Freedom Meditech, Inc., San Diego, CA (US)

( * ) Notice: Subject to any disclaimer, the term of this patent is extended or adjusted under 35 U.S.C. 154(b) by 263 days.

(21) Appl. No.: 13/291,072

(22) Filed: Nov. 7, 2011

(65) Prior Publication Data

US 2012/0203086 A1 Aug. 9, 2012

Related U.S. Application Data

(60) Provisional application No. 61/410,825, filed on Nov. 5, 2010, provisional application No. 61/410,827, filed on Nov. 5, 2010, provisional application No. 61/410,830, filed on Nov. 5, 2010, provisional application No. 61/410,831, filed on Nov. 5, 2010, provisional application No. 61/410,833, filed on Nov. 5, 2010, provisional application No. 61/410,834, filed on Nov. 5, 2010, provisional application No. 61/410,835, filed on Nov. 5, 2010, provisional application No. 61/410,839, filed on Nov. 5, 2010.

(51) Int. Cl.
*A61B 5/00* (2006.01)
*A61B 3/117* (2006.01)
*A61B 5/145* (2006.01)
*A61B 5/1455* (2006.01)
*G01N 21/64* (2006.01)
*G01N 21/65* (2006.01)

(52) U.S. Cl.
CPC ............. *A61B 3/1173* (2013.01); *A61B 5/0071* (2013.01); *A61B 5/14546* (2013.01); *A61B 5/1455* (2013.01); *A61B 5/4842* (2013.01); *G01N 21/6486* (2013.01); *G01N 21/65* (2013.01); *G01N 2800/042* (2013.01)
USPC ........................... 600/476; 600/407; 600/473

(58) Field of Classification Search
USPC ......................................... 600/407, 473–476
See application file for complete search history.

(56) References Cited

U.S. PATENT DOCUMENTS 3,432,227 A 3/1969 Soper
4,685,784 A 8/1987 Kirchhuebel
(Continued)

FOREIGN PATENT DOCUMENTS

EP 1 913 866 A1 4/2008
WO WO 2005/045393 A2 5/2005
(Continued)

OTHER PUBLICATIONS

Bang et al., "Development and Validation of a Patient Self-assessment Score for Diabetes Risk", *Ann Intern Med*, 151:775-783 (2009).
(Continued)

*Primary Examiner* — Peter Luong
(74) *Attorney, Agent, or Firm* — DLA Piper LLP (US)

(57) ABSTRACT

Apparatus and methods for spectroscopic analysis of biological tissues to classify an individual as diabetic or non-diabetic, or to determine the probability, progression or level of a disease or medical condition in an individual.

9 Claims, 13 Drawing Sheets

(56) References Cited

U.S. PATENT DOCUMENTS

| | | |
|---|---|---|
| 4,848,899 A | 7/1989 | Kobayashi et al. |
| 4,883,351 A | 11/1989 | Weiss |
| 4,895,159 A | 1/1990 | Weiss |
| 5,035,500 A | 7/1991 | Rorabaugh et al. |
| 5,203,328 A | 4/1993 | Samuels et al. |
| 5,442,412 A | 8/1995 | Frey et al. |
| 5,582,168 A | 12/1996 | Samuels et al. |
| 5,882,301 A | 3/1999 | Yoshida |
| 5,947,955 A | 9/1999 | Kadambi et al. |
| 6,004,313 A | 12/1999 | Shimmick et al. |
| 6,088,606 A | 7/2000 | Ignotz et al. |
| 6,704,588 B2 | 3/2004 | Ansari et al. |
| 6,869,427 B1 | 3/2005 | Shokoohi |
| 7,001,018 B1 | 2/2006 | Martin |
| 7,043,288 B2 | 5/2006 | Davis, III et al. |
| 7,139,598 B2 | 11/2006 | Hull et al. |
| 2007/0243521 A1 | 10/2007 | Zuckerman et al. |
| 2009/0143685 A1 | 6/2009 | Elner et al. |

FOREIGN PATENT DOCUMENTS

| | | |
|---|---|---|
| WO | WO 2006/009906 A2 | 1/2006 |
| WO | 2012/061835 | 5/2012 |
| WO | 2012/061836 | 5/2012 |

OTHER PUBLICATIONS

Diabetes Prevention Program Research Group, "Reduction in the Incidence of Type 2 Diabetes With Lifestyle Intervention Or Metformin", *NEJM*, 346(6):393-403 (2002).

ADA Committee Report, "Report of the Expert Committee on the Diagnosis and Classification of Diabetes Mellitus", *Diabetes Care* (2003).

Cornell Chronicle: Diabetes tool screens for disease in adults, from the internet, Dec. 21, 2009 http://www.news.cornell.edu/stories/Dec09/NYCdiabetes.hmtl.

APPARATUS AND METHOD FOR NON-INVASIVELY DETECTING DISEASES THAT AFFECT STRUCTURAL PROPERTIES IN BIOLOGICAL TISSUES

CROSS-REFERENCE TO RELATED APPLICATIONS

This application is related to, and claims the benefit of, U.S. Provisional Patent Application Nos. 61/410,825, 61/410,827, 61/410,830, 61/410,831, 61/410,833, 61/410,834, 61/410,835, and 61/410,839, each of which was filed on Nov. 5, 2010, and each of which is incorporated herein by reference in its entirety.

Concurrently filed herewith on the same day is a co-pending non-provisional patent application also claiming the benefit of each of the above-identified U.S. Provisional Patent Applications, which is entitled, "IMPROVED ALGORITHM FOR DETECTION OF DIABETES," assigned to U.S. patent application Ser. No. 13/291,074, and having at least one common inventor. The disclosure of the concurrently filed patent application is hereby incorporated by reference in its entirety.

BACKGROUND

Non-invasive devices and methods for detecting disease, such as diabetes, are described. In particular, the exemplary embodiments relate to methods and apparatuses suitable for determining in a mammal the presence, likelihood, progression and/or severity of diabetes mellitus.

Diabetes mellitus ("diabetes") is a group of metabolic diseases in which a person has high blood sugar (hyperglycemia), either because the body does not produce enough insulin, or because the body's cells do not respond to the insulin that is produced. Diabetes is a disease derived from multiple causative factors and characterized by elevated levels of plasma glucose in the fasting state or after administration of glucose during an oral glucose tolerance test (OGTT). There are two primary forms of diabetes mellitus: (1) insulin dependent or Type 1 diabetes (a.k.a., Juvenile Diabetes, Brittle Diabetes, Insulin Dependent Diabetes Mellitus (IDDM)) and (2) non-insulin-dependent or Type II diabetes (a.k.a., NIDDM). Type 1 diabetes develops most often in young people, but can appear in adults that have the same auto anti body as the Type 1. Type 2 diabetes develops most often in middle aged and older adults, but can appear in young people. This high blood sugar condition produces symptoms of polyuria (frequent urination), polydipsia (increased thirst) or polyphagia (increased hunger). Diabetes is a large and growing problem throughout the world's developed and developing nations. As of now, it has been forecasted that approximately one in 10 U.S. adults have diabetes and according to a Centers for Disease Control and Prevention report, cases of diabetes are projected to double, even triple, by 2050 with as many as one in three having the disease, primarily type 2 diabetes.

Insulin is a hormone produced in the pancreas by β-cells. The function of insulin is to regulate the amount of glucose (sugar) in the blood, which enters cells through receptors that accept insulin and allow glucose to enter. Once inside a cell, glucose can be used as fuel. Excess glucose is stored in the liver and muscles in a form called glycogen. When blood glucose levels are low, the liver releases glycogen to form glucose. Without insulin, glucose has difficulty entering cells. In persons with diabetes mellitus, the pancreas either produces no insulin, too little insulin to control blood sugar, or defective insulin. Without insulin, these symptoms progress to dehydration, resulting in low blood volume, increased pulse rate, and dry, flushed, skin. In addition, ketones accumulate in the blood faster than the body is able to eliminate them through the urine or exhaled breath. Respiration becomes rapid and shallow and breath has a fruity odor. Other symptoms indicating a progression towards diabetic ketoacidotic coma (DKA) include vomiting, stomach pains, and a decreased level of consciousness. Persons with diabetes are at increased risk for debilitating complications such as renal failure, blindness, nerve damage and vascular disease. Although risk for or progression of complications can be reduced through tight glucose control combined with drug therapy and lifestyle changes, effective mitigation of complications begins with early detection. The disease leads to serious complications, including hyperglycemia, macroangiopathy, microangiopathy, neuropathy, nephropathy and retinopathy. As a result, diabetes adversely affects the quality of life. Similarly, uncontrolled Type 2 diabetes leads to excess glucose in the blood, resulting in hyperglycemia, or high blood sugar.

A person with Type 2 diabetes experiences fatigue, increased thirst, frequent urination, dry, itchy skin, blurred vision, slow healing cuts or sores, more infections than usual, numbness and tingling in feet. Without treatment, a person with Type 2 diabetes will become dehydrated and develop a dangerously low blood volume. If Type 2 diabetes remains uncontrolled for a long period of time, more serious symptoms may result, including severe hyperglycemia (blood sugar over 600 mg) lethargy, confusion, shock, and ultimately "hyperosmolar hyperglycemic non-ketotic coma." Persistent or uncontrolled hyperglycemia is associated with increased and premature morbidity and mortality. As such, therapeutic control of glucose homeostasis, lipid metabolism, obesity, and hypertension are critically important in the clinical management and treatment of diabetes mellitus.

Pre-diabetes (i.e. where no overt clinical signs of diabetes are displayed) can be present for seven or more years before the detection of glycemic abnormalities and after disease onset and early stage diabetic complications are presented or diagnosed. More aggressive screening of individuals at risk for diabetes is needed. A major reason is that no simple and unambiguous laboratory test has existed that can be used to identify those subjects at risk for developing diabetes or pre-diabetes. There also is a need to identify subjects with a diabetic condition, including both pre-diabetic and diabetic subjects, so that they can obtain treatment early, and also to monitor the progression of the disease over time non-invasively. Early diagnosis, intensive treatment and consistent long-term follow-up evaluations for diabetic patients are essential for effective care, which can help preserve vision and significantly lower the risk of blindness. The diabetes Control and Complications Trial, (DCCT) in the USA demonstrated if a diabetic can be detected and brought under glucose control, complications can be reduced, e.g., (retinopathy) by eighty percent (80%). Once it becomes apparent that a patient may possibly develop diabetes, doctors are trained to ask the patient to return for more tests on a periodic basis to determine whether the patient's condition actually develops into the disease. Doctors have certain protocols about how long a patient should wait before being recalled for more testing. If a patient has few symptoms suggestive of diabetes, the patient may not be recalled from more than a year. If several suggestive symptoms are present, the doctor may wish to recall the patient after only a few months. Unfortunately, there is no diagnostic tool for accurately predicting how long a patient may have been experiencing diabetic symptoms, or for determining how great the patient's risk of actually developing the disease. If such a tool were available, it would enable a doctor to tailor his recall and therapy pattern to a patient's needs.

Modern diabetes screening and monitoring is a particularly "puncture-intensive" because diabetics have to draw blood to test their glucose levels. The only practical, reliable screening method currently available for monitoring blood glucose is by means of blood sampling. The primary screening and diagnostic tests currently in use—the Fasting Plasma Glucose (FPG) and the Oral Glucose Tolerance Test (OGTT)—are not considered to be optimum because they are inconvenient and unpleasant. Both require venous draws and are fasting tests so they can only be practically administered during morning appointments and are prone to non-compliance issues. For the OGTT, the measurement occurs two (2) hours after the patient ingests a 75 g oral glucose load. Numerous studies have evaluated the performance of each of these tests in diverse populations. It is believed that approximately one-half of those with diabetes are misclassified by a single FPG test. In addition, it is believed that the OGTT suffers from relatively poor reproducibility. In addition, the HbA1c test reflects longer term 90 day glycaemia and control or lack of control than FPG does, the results of the test can also be distorted due to recent changes in diet or hemolytic conditions. Such blood glucose measurement methodologies have limited value as indices of long-term glycemic status. In summary, blood glucose measurements (such as HbA1c and FPG) have limited value as reliable indices of long-term glycemic status.

Consequently, a rapid, accurate, reliable and convenient and non-invasive screening test is needed as a viable alternative to current tests. Ideally, an improved screening test would measure an analyte that is directly related to progression of the disease and the risk of complications, and the chemical marker would be invariant to within- or between-day changes in the patient as an integrated biomarker. In addition, the measurement should offer sufficient accuracy to detect diabetes in its early stages and possess adequate precision to eliminate the requirement for repeat, confirmatory testing. Once it becomes apparent that a patient may possibly have diabetes, doctors and optometrists will ask the patient to return for more tests on a periodic basis to determine whether the patient's condition actually develops into the disease or is confirmed to be diabetes. There are certain protocols about how long a patient should wait before being recalled for more testing. If a patient has few symptoms suggestive of diabetes, then the patient may not be recalled for more than a year. If several suggestive symptoms are present, then the patient may be recalled after only a few months. It would be useful if there was available a diagnostic tool and methods for non-invasively and accurately determining whether a patient is at risk of actually developing diabetes or actually has diabetes for immediate confirmation.

A major consequence of hyperglycemia is excessive glycosylation (non-enzymatic glycation) of proteins in a process known as the Maillard reaction. Excessive glycosylation eventually causes the formation of various protein-protein cross-links and non-crosslinked structures called Advanced Glycation End-products (AGEs). AGEs are believed to present an attractive candidate analyte for non-invasive measurements. AGEs have been implicated as causal factors in the complications of diabetes, including diabetic retinopathy (DR). Protein glycation is a multi-stage reaction that begins with formation of a sugar adduct to protein, known as a fructosamine or Amadori compound, which gradually matures to form AGEs. Some AGEs require oxidation chemistry for their formation and are known as glycoxidation products. Collagen is a protein that readily undergoes glycation and glycoxidation. Because of its long half-life, the level of AGEs in collagen is believed to act as a long-term integrator of overall glycemia that is insensitive to short- or intermediate-term fluctuations in glycemic control. As a result, AGEs accumulate naturally during healthy aging, but at significantly accelerated rates in persons with diabetes. Protein glycation and AGE formation are accompanied by increased free radical activity that contributes to the biomolecular damage in diabetes. Levels of AGEs are positively correlated with the severity of retinopathy, nephropathy and neuropathy and, as such are an indicator of systemic damage to protein in diabetes and a metric of a patient's risk for diabetic complications. In addition, due to the mild to severe hyperglycemia associated with pre-diabetes and type 2 diabetes, individuals who are in the early stages of this continuum will accumulate AGEs at higher than normal rates in their tissues. Thus, given sufficient assay sensitivity, an accurate AGE measurement in an individual offers the promise to detect early departure from normal glycemia. Currently, AGEs are assayed by invasive procedures requiring a biopsy specimen, and consequently are not used in diabetes screening or diagnosis.

Tissue such as the ocular lens can exhibit fluorescence when excited by a light source of a suitable wavelength. This fluorescence emission, arising from endogenous fluorophores, is an intrinsic property of the tissue and is called autofluorescence to be distinguished from fluorescent signals obtained by adding exogenous markers (like sodium fluorescein). The tissue fluorophores absorb certain wavelengths of light (excitation light), and release it again in light of longer wavelengths (emission). Several tissue fluorophores have been identified, such as collagen, elastin, lipofuscin, NADH, porphyrins and tryptophan. Each fluorophore has its characteristic excitation and emission wavelength, that enables localization and further quantification of a particular fluorophore. Autofluorescence can be induced in several tissues and can therefore be applied in investigation of several diseases. It is also used to distinguish malignant from benign tissue in several tissues, such as the skin and cervix. Furthermore, in ophthalmology, autofluorescence of the lens increases with ageing and diabetes. Autofluorescence of the lens appears to be caused by glycation and, subsequent oxidation of lens crystalline, which forms AGEs. The crystalline lens represents an exceptional bio target since the proteins in the lens are relatively static for life and do not turn over (i.e., undergo reverse glycation) allowing for the accumulation of AGEs.

Advances in fluorescence spectroscopy of the ocular lens has revealed a potential for a non-invasive device and method to sensitively measure changes in the lens of the eye associated with diabetes mellitus. The system relies on the detection of the spectrum of fluorescence emitted from a selected volume (about $\frac{1}{10}$ mm$^3$ to about 3 mm$^3$ or more) of the lens of living human subjects using low power excitation illumination from monochromatic light sources. The sensitivity of this technique is based on the measurement of the fluorescence intensity in a selected region of the fluorescence spectrum and normalization of this fluorescence with respect to attenuation (scattering and absorption) of the incident excitation light. The amplitude of the unshifted Rayleigh line, measured as part of the fluorescence spectrum, is used as a measure of the attenuation of the excitation light in the lens. Using this methodology it is believed that the normalized lens fluorescence provides a more sensitive discrimination between diabetic and non-diabetic lenses than more conventional measurements of fluorescence intensity from the lens. Results from such clinical measurements could be used to describe a relationship between normalized lens fluorescence and hemoglobin A1c levels in diabetic patients.

Optical spectroscopy offers one potential avenue of early, non-invasive detection of diabetes by quantifying AGEs in the lens of the eye or other tissues. In spectroscopy, a machine fires a laser or other light on the skin or in the eye. Fluorescence spectroscopy (a.k.a. fluorometry or spectrofluorometry), is a type of electromagnetic spectroscopy that analyzes fluorescence from a sample by detecting the presence of certain molecules by measuring their reflected or emitted light. In fluorescence spectroscopy, the species is first excited, by absorbing a photon, from its ground electronic state to one of the various vibrational states in the excited electronic state. Collisions with other molecules cause the excited molecule to lose vibrational energy until it reaches the lowest vibrational state of the excited electronic state. The molecule then drops down to one of the various vibrational levels of the ground electronic state again, emitting a photon in the process. As different molecule species may drop down from different vibrational levels to the ground state, the emitted photons will have different energies, and thus frequencies. Those photons that are reflected from particles surfaces or refracted through them are called "scattered". Scattered photons may encounter another grain or be scattered away from the surface so they may be detected and measured. Every molecule has a signature structure that reflects light at a specific wavelength; all glucose molecules share a unique signature that's entirely different from other blood components such as hemoglobin. If the returning wavelength differs from an established norm, the device alerts the patient or doctor to the presence of the molecule or cell in question. Therefore, by analyzing the different frequencies of light emitted in fluorescent spectroscopy, along with their relative intensities, the structure of the different vibrational levels can be determined.

Fluorescence-based systems rely on the propensity of certain cell components, known as fluorophores (e.g., tryptophan, flavins, collagen), to emit light when excited by specific wavelengths of light, with the peak intensity in a different, but corresponding frequency band. The actual amount of light emitted by fluorophores is exceedingly small (on the order of nanowatts) requiring an extremely sensitive photodetection system. The basic function of an optical spectroscopy device is to irradiate the specimen with a desired and specific band of wavelengths, and then to separate the much weaker emitted fluorescence from the excitation light. Only the emission light should reach the eye or detector so that the resulting fluorescent structures are superimposed with high contrast against a very dark (or black) background. The limits of detection are generally governed by the darkness of the background, and the excitation light is typically several hundred thousand to a million times brighter than the emitted fluorescence.

If AGEs are illuminated by light from 300-500 nm, then 400-700 nm fluorescence is emitted. Certain early metabolic changes may be detected by fluorescence spectroscopy as AGEs develop. Reflectance techniques attempt to characterize tissue by measuring the amount and wavelengths of light reflected back to a sensitive photodetector when the tissue (e.g., lens of the eye) is exposed to a light source. Fluorescence and reflected light measurements are analyzed using computer-based algorithms; however, these systems have not been studied extensively. Non-invasive ocular fluorescence measurements have been investigated on numerous occasions for diabetes screening and AGE quantitation.

For example, autofluorescence of the lens of the eye can be measured with a computer fluorophotometer (Fluorotron Master, Coherent Radiation Inc. (Palo Alto, Calif.)) fitted with a special lens ("anterior segment adapter") for detailed scanning of lens. Autofluorescence of the lens, excited by a beam of continuous blue light can be scanned along the optical axis by moving the internal lens system of the fluorophotometer by a computer-controlled motor. The wavelengths of excitation and fluorescent light can be set by color filters with peak transmission at 490 nm and 530 nm respectively. The measured autofluorescence, expressed in equivalents of fluorescein concentration can be recorded as a function of distance in the eye.

It is always desirable to detect diseases early in their progress. In particular, it is desirable to screen and start treating glucose-intolerant individuals as early as possible since, even before the onset of diabetes, vascular lesions gradually develop with deterioration of glucose tolerance. Additionally, beta-cell function is seriously compromised by the time that overt alterations in glucose homeostasis, such as impaired glucose tolerance (IGT) and impaired fasting glucose (IFG), are manifest; thus, timely intervention is important to maintain residual insulin secretory capacity. Early detection enables early treatment which is generally believed to yield a higher success rate in treating various diseases. Recently, it is believed that analyzing eyes, and in particular the lenses of the eyes, can yield indications of various types of diseases. For example, measurements taken of light scattering within the eye has been shown to provide useful diagnostic information to detect and monitor the progress of diseases. Since this region is up to a few millimeters thick, measurements of this region, to be useful, need to be very accurate in the information for the position of the measurement. This is especially true because the human eye is in almost constant motion even when a patient is fixating on an illuminated target. This is particularly true because eye care professionals, such as optometrists, regularly examine, diagnose, treat and manage diseases, injuries, and disorders of the eyes and associated structures, as well as identify related systemic conditions affecting the eye. Optometrists, through their clinical education and experience, and broad geographic distribution, and the means to provide primary eye and vision care for the public. There often the first healthcare practitioners to examine patients with undiagnosed diabetes or ocular manifestations of diabetes.

The effectiveness of early intervention with lifestyle modification or medication in arresting disease progression has been demonstrated by the Diabetes Prevention Program (Diabetes Prevention Program Research Group. NEJM 346:393-403, 2002). However, the determination of IGT and IFG is itself an issue due to the relatively invasive nature of these assessments, particularly that of IGT by an oral glucose tolerance test (OGTT). In addition, an important additional diagnostic problem is monitoring of glucose homeostasis for confirming diabetes. Compliance with glucose monitoring is poor because of the pain and inconvenience of conventional blood collection using lancets. Furthermore, non-invasive monitoring techniques for diabetes, and to determine the efficacy of therapy, are desirable. Finally, assessment of progression of frank diabetes to complications is only feasible after complications are well established. Thus, it would be beneficial to have methods for assessing the development of diabetes from pre-diabetes, and for monitoring the course of the disease.

There is known at least one attempt to produce a commercial grade non-invasive diabetes detection/screening device that measures crystalline lens fluorescence, known as the Accu-Chek D-Tector. The Accu-Chek-D-Tector is essentially a confocal microscope in that it uses confocal optics to measure AGEs to check for early signs of uncontrollable blood sugar levels and type 2 diabetes because they build up more quickly in the eyes of individuals with high blood sugar levels than in the eyes of individuals with normal levels. The device employs so called biophotonic technology and detects diabetes by shining a blue light into the lens of the eye of a patient. The returned light is collected and analyzed. The light emitted from the eye of a person with diabetes is more intense than that of a person without diabetes. In particular, a laser beam passes through a light source aperture and then is focused by an objective lens into a small (ideally diffraction limited) focal volume within or on the surface of a patient's eye. Scattered and reflected laser light as well as any fluorescent light from the illuminated spot is then re-collected by the objective lens (collector). A beam splitter separates off some portion of the light into a detection apparatus, which in fluorescence confocal microscopy may have a filter that selectively passes the fluorescent wavelengths while blocking the original excitation wavelength. After optionally passing through a pinhole, the light intensity is detected by a photo-detection device (e.g., a photomultiplier tube (PMT)), transforming the light signal into an electrical one that is recorded by a computer for further analysis. In particular, the Accu-Chek D-Tector shines a blue light into the lens of the eye, then collects and analyzes the returned light.

However, major drawbacks of the Accu-Chek-D-Tector are that it is relatively slow, imprecise and costly to manufacture. Although the device could purportedly take readings in 30 seconds (15 seconds for fluorescence, 15 seconds for backscatter) to obtain a ratio of fluorescence signal to back-scattered signal from a specific location within the patient's lens, the device employed a sliding filter changer to select either green (fluorescence) or blue (backscattered) light striking a photodetector via a crank mechanism. Rotation of a step motor actuated the two position slider taking one or more seconds to move from one filter to the other. In addition, in use, the patient was required to self-align to the device via a fixation system that made it difficult and time-consuming.

Most non-invasive analyzers are not designed specifically for high-throughput screening purposes. They are difficult and expensive to integrate into a high-throughput screening environment. Even after the analyzer is integrated into the high-throughput screening environment, there often are many problems, including increased probability of system failures, loss of data, time delays, and loss of costly compounds and reagents. Thus, prior non-invasive diabetes detection devices generally have not recognized the need to provide analytic flexibility and high performance.

Typically, a non-invasive apparatus uses some form of spectroscopy to acquire the signal or spectrum from the body. Spectroscopic techniques include but are not limited to Raman and Rayleigh fluorescence, as well as techniques using light from ultraviolet through the infrared [ultraviolet (200 to 400 nm), visible (400 to 700 nm), near-infrared (700 to 2500 nm or 14,286 to 4000 cm-1), and infrared (2500 to 14,285 nm or 4000 to 700 cm-1)]. It is important to note, that these techniques are distinct from the traditional invasive and alternative invasive techniques listed above in that the sample analyzed is a portion of the human body in-situ, not a biological sample acquired from the human body.

A real need exists for a versatile, sensitive, high-throughput screening apparatus and methods that can handle multiple detections and wide ranges of patients while reliably maintaining a high level of sensitivity. In addition to early identification, it there is a need for diabetes detection apparatus, devices, methods and/or systems for detecting diabetes that requires no fasting and is a cumulative test that is not exposed to variations in glucose levels caused from a variety of reasons, including food, stress certain drugs, or short term changes in diet and exercise.

BRIEF DESCRIPTION OF THE DRAWINGS

The accompanying drawings, which are incorporated in and constitute a part of the specification and written description, illustrate exemplary embodiments and, together with the written description, serve to exemplify principles of the claims.

DESCRIPTION OF EXEMPLARY EMBODIMENTS

Figure 1:
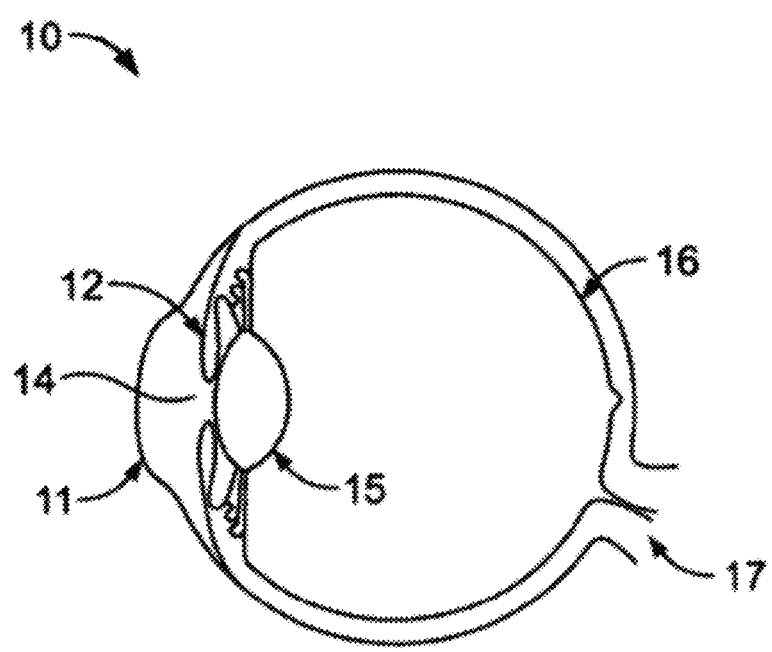
FIG. 1 shows a side view cross-section of an eye and its constituent parts.
Figure 2:
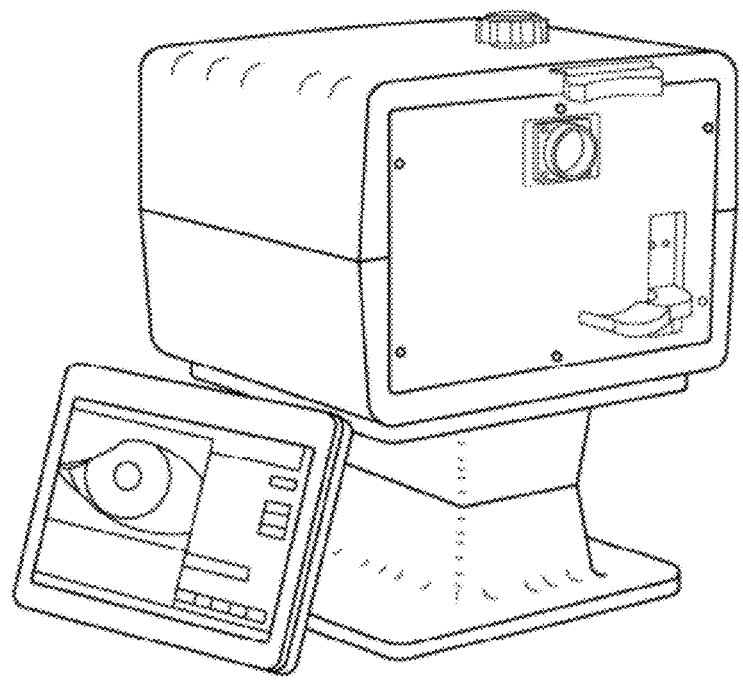
FIGS. 2 and 2A depict perspective and front views, respectively, of an example embodiment showing external parts.
Figure 2A:
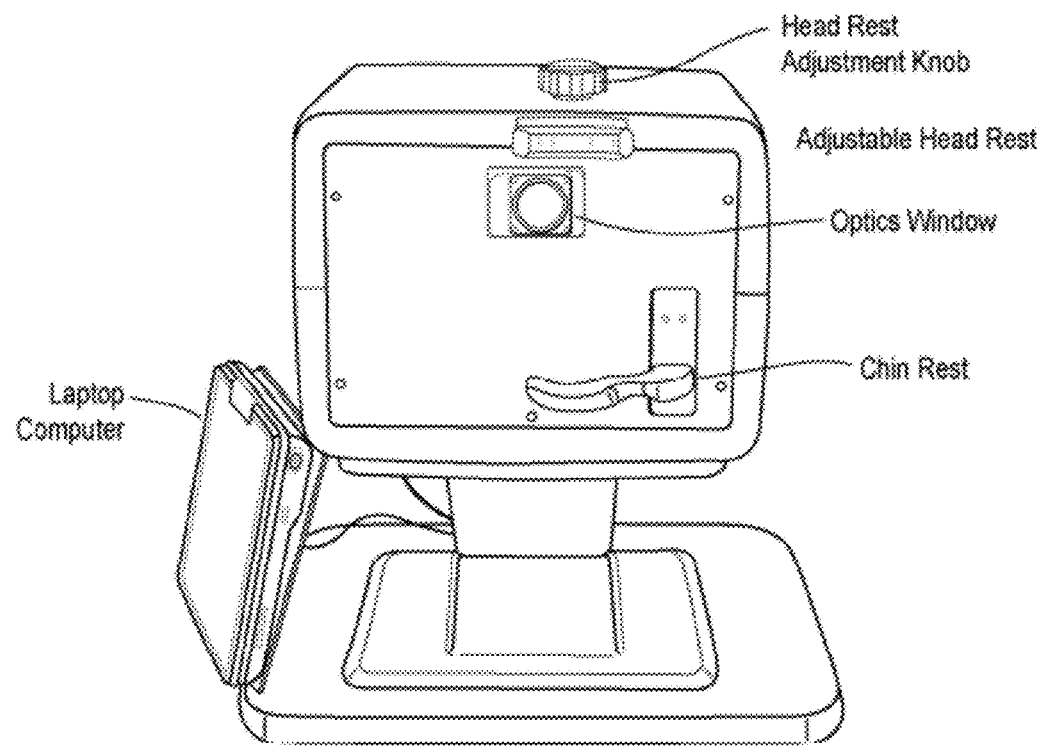
Figure 3:
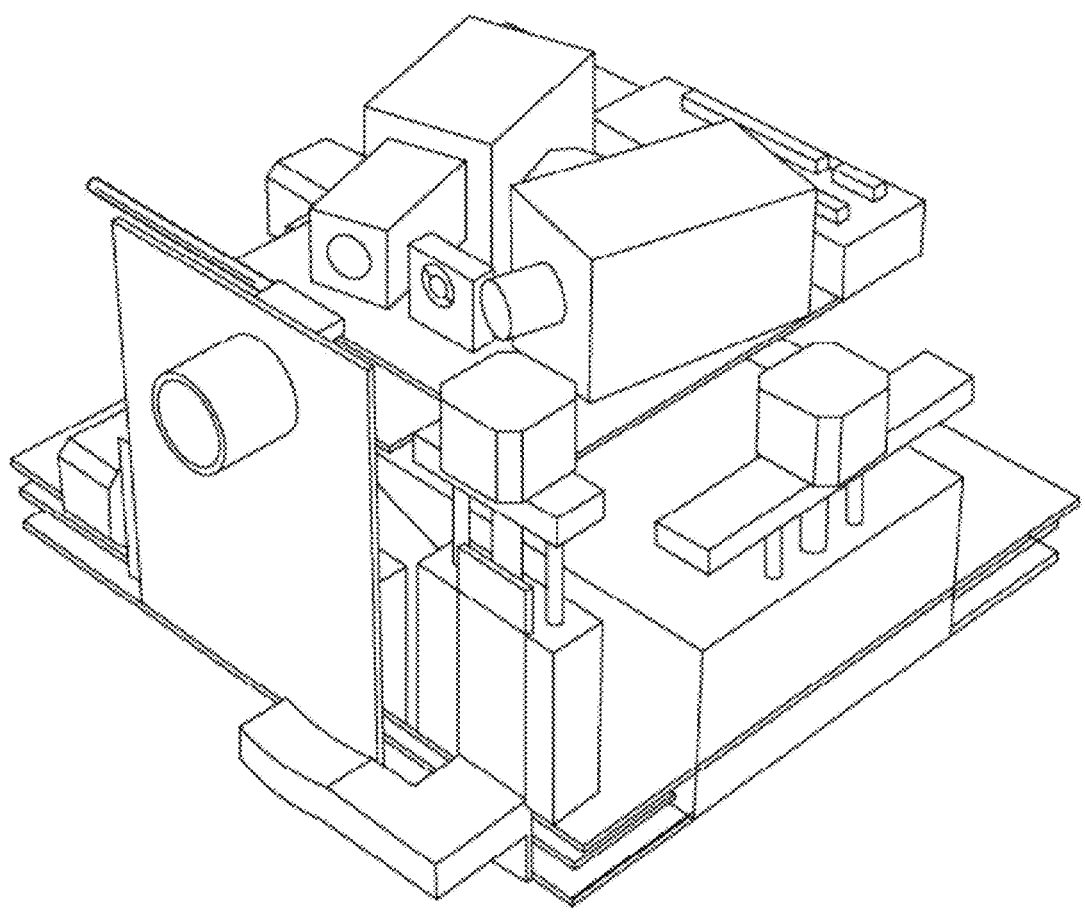
FIGS. 3 and 3A depict perspective views (unlabeled and labeled, respectively) of an example embodiment showing internal parts.
Figure 3A:
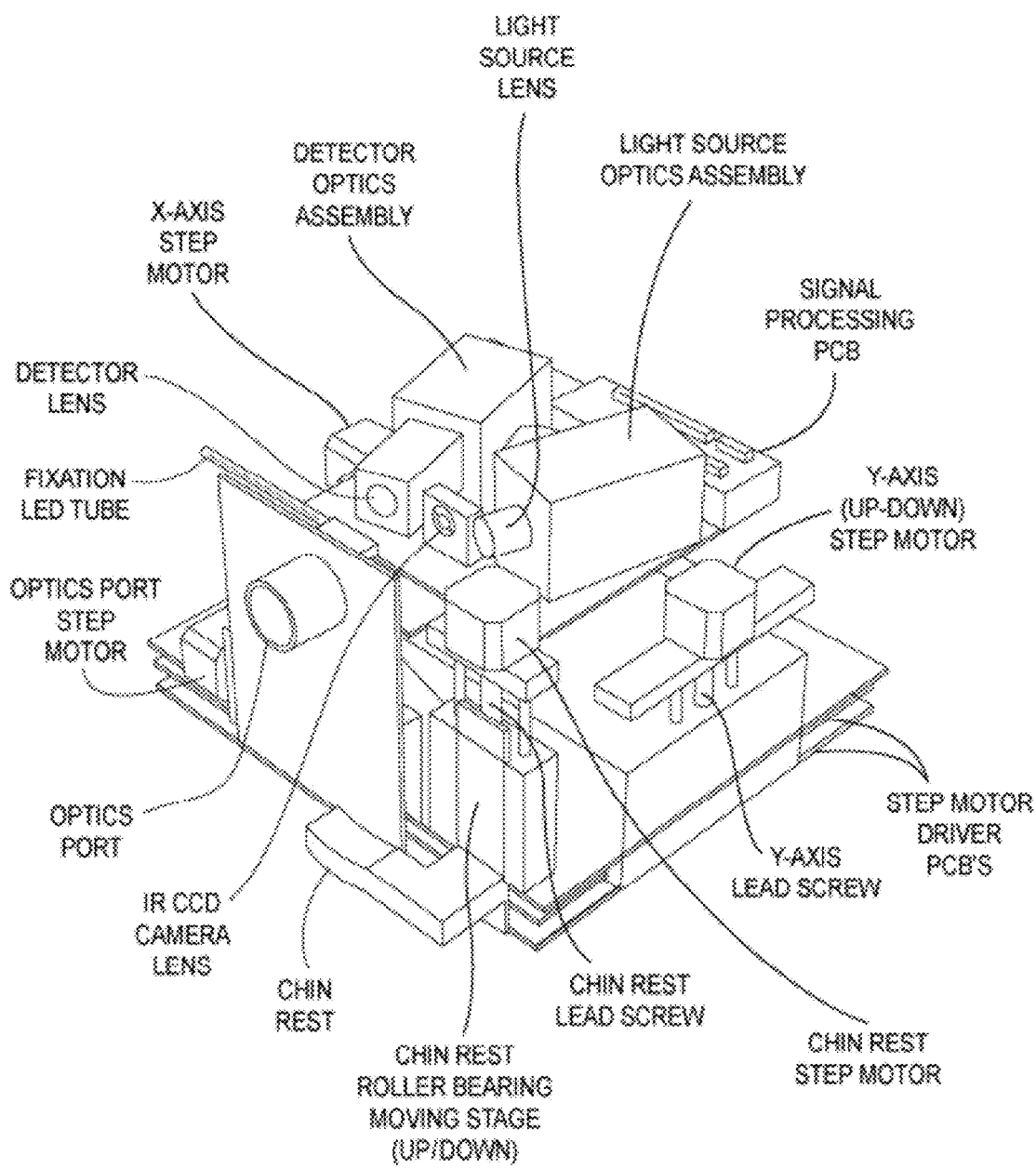
Figure 4:
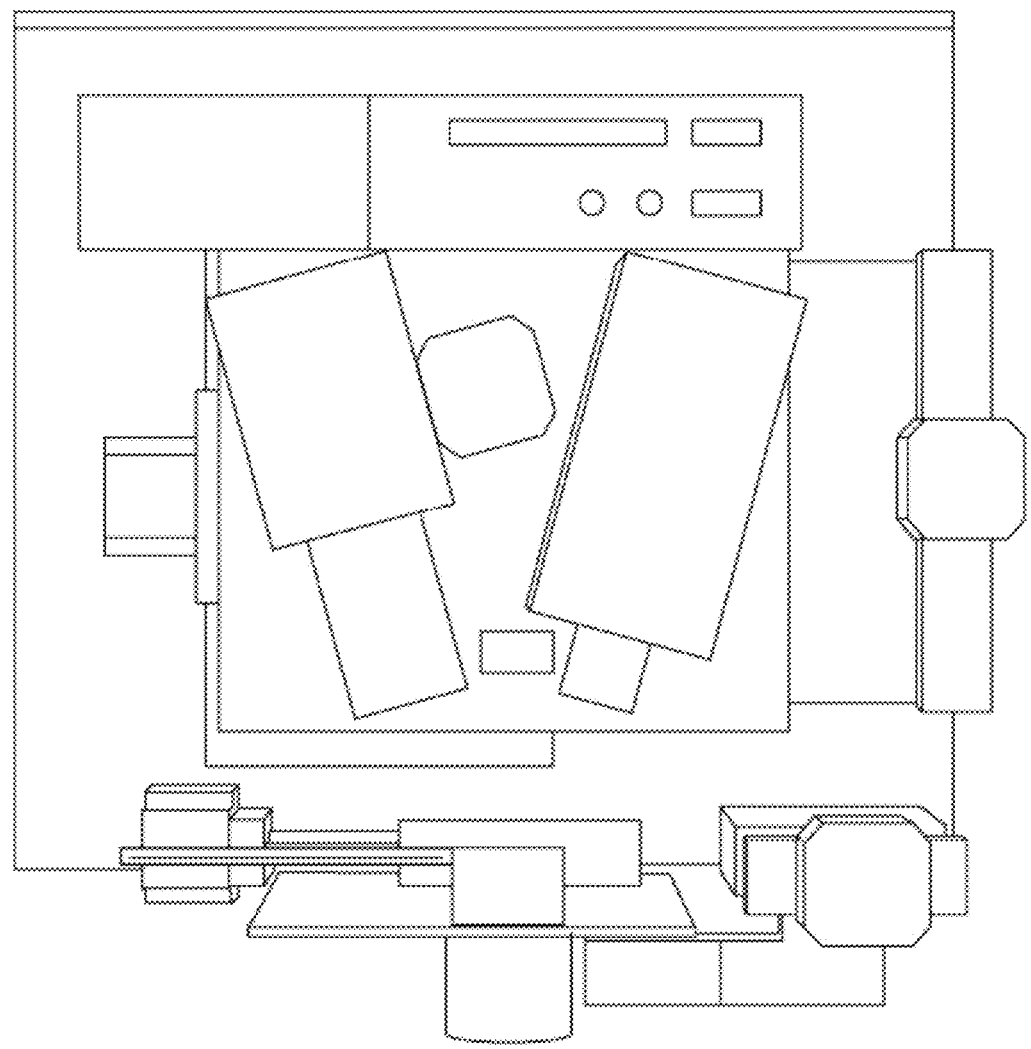
FIGS. 4 and 4A depict top views (unlabeled and labeled, respectively) of an example embodiment showing internal parts.
Figure 4A:
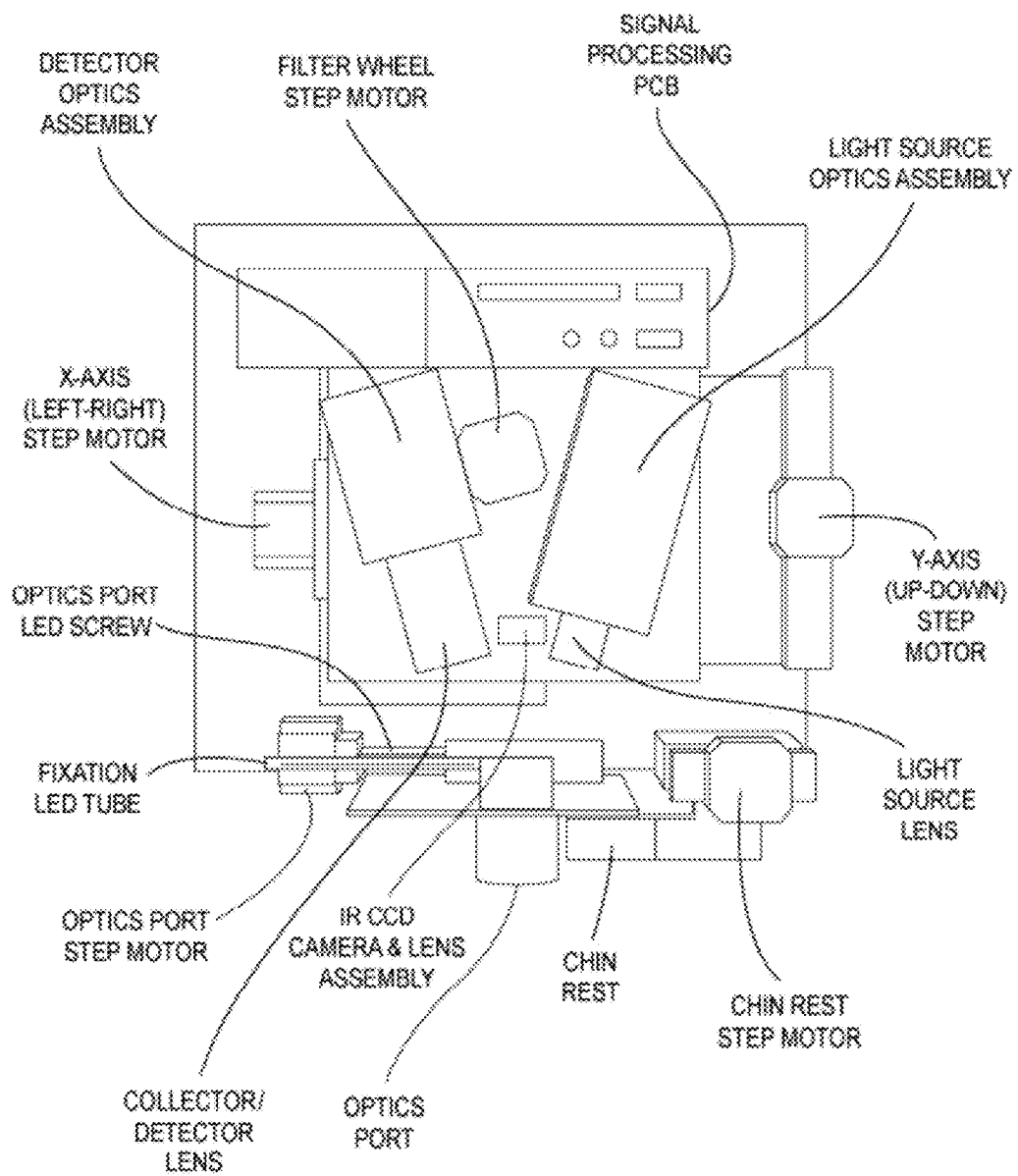
Figure 5:
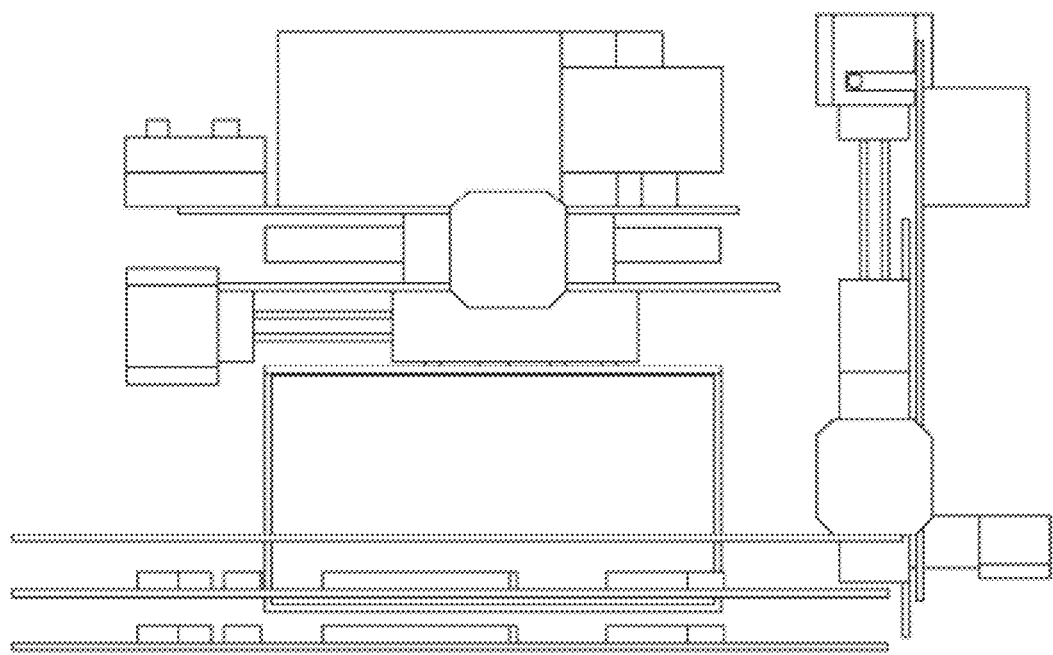
FIGS. 5 and 5A depict side views (unlabeled and labeled, respectively) of an example embodiment showing internal parts.
Figure 5A:
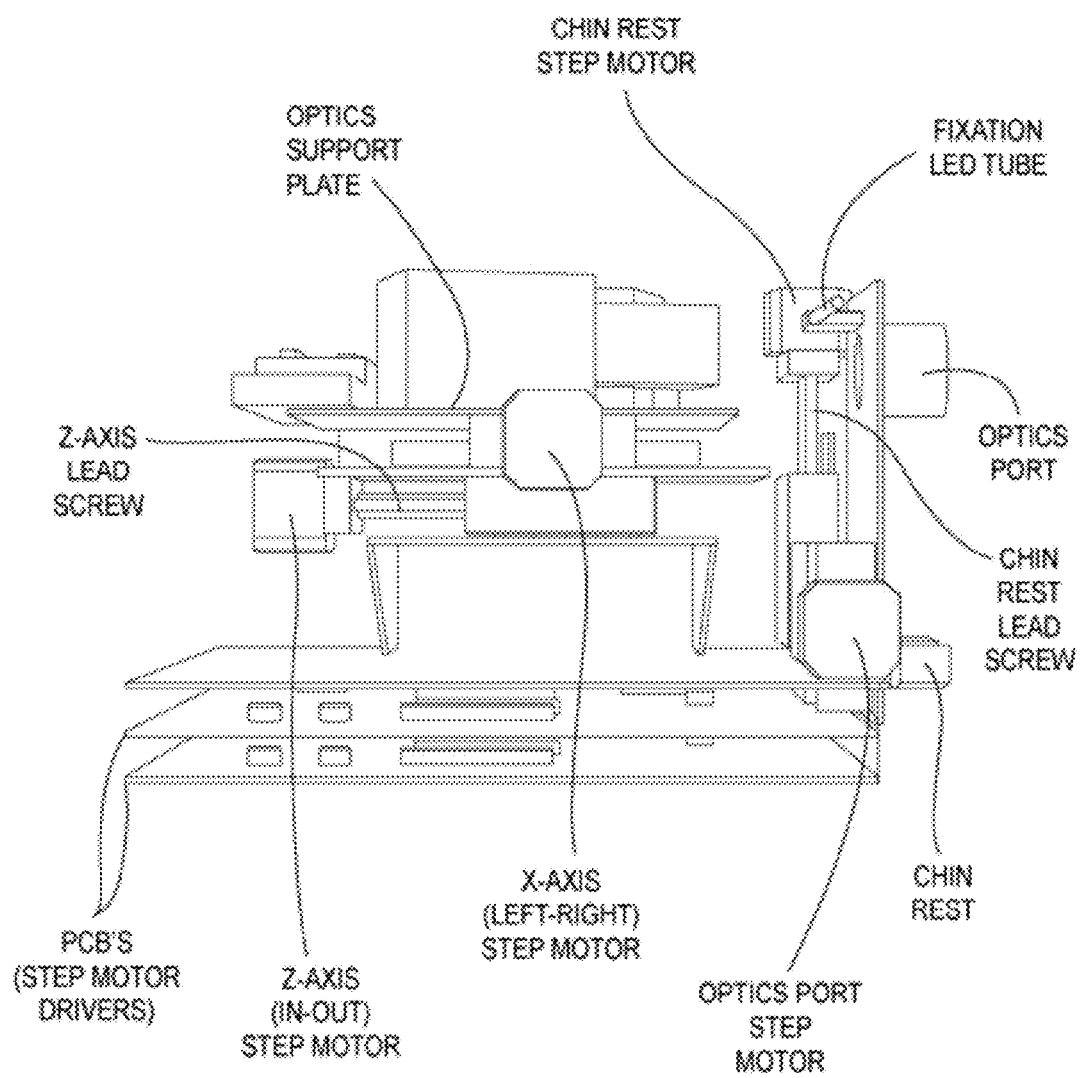

Various exemplary embodiments of an invention are now described with or without reference to a Figure, where like references indicate identical or functionally similar elements. The example embodiments, as generally described and illustrated in the Figures herein, could be arranged and designed in a wide variety of different configurations. Thus, the following more detailed description of exemplary embodiments, as described and/or represented in the Figures, is not intended to limit the scope of the subject matter claimed, but is merely representative of the exemplary/example embodiments.

Certain aspects, advantages, and novel features are shown in the Figures and/or described herein. It is to be understood that not necessarily all such aspects, advantages, and features expressly or inherently discussed herein may or may not be employed and/or achieved in accordance with any particular embodiment or aspect thereof. Thus, for example, those skilled in the art will recognize that an exemplary embodiment may be carried out in a manner that achieves one advantage or group of advantages as taught or inferred herein without necessarily achieving other advantages as may be taught or suggested herein. Of course, advantages not expressly taught or inferred herein may be realized in one or more exemplary embodiments.

Except as otherwise expressly provided, the following rules of interpretation apply to this specification (written description, claims and drawings): (a) all words used herein shall be construed to be of such gender or number (singular or plural) as the circumstances require; (b) the singular terms "a", "an", and "the", as used in the specification and the appended claims include plural references unless the context clearly dictates otherwise; (c) the antecedent term "about" applied to a recited range or value denotes an approximation within the deviation in the range or value known or expected in the art from the measurements method; (d) the words "herein", "hereby", "hereof", "hereto", "hereinbefore", and "hereinafter", and words of similar import, refer to this specification in its entirety and not to any particular paragraph, claim or other subdivision, unless otherwise specified; (e) descriptive headings are for convenience only and shall not control or affect the meaning or construction of any part of the specification; and (d) "or" and "any" are not exclusive and "include" and "including" are not limiting. Further, The terms "comprising," "having," "including," and "containing" are to be construed as open-ended terms (i.e., meaning "including, but not limited to,") unless otherwise noted.

Recitation of ranges of values herein are merely intended to serve as a shorthand method of referring individually to each separate value falling within the range, unless otherwise indicated herein, and each separate value is incorporated into the specification as if it were individually recited herein. Where a specific range of values is provided, it is understood that each intervening value, to the tenth of the unit of the lower limit unless the context clearly dictates otherwise, between the upper and lower limit of that range and any other stated or intervening value in that stated range, is included therein. All smaller sub ranges are also included. The upper and lower limits of these smaller ranges are also included therein, subject to any specifically excluded limit in the stated range.

Unless defined otherwise, all technical and scientific terms used herein have the same meaning as commonly understood by one of ordinary skill in the relevant art. Although any methods and materials similar or equivalent to those described herein can also be used, the preferred methods and materials are now described.

As used herein, the terms "an embodiment", "embodiment", "embodiments", "the embodiment", "the embodiments", "one or more embodiments", "some embodiments", "certain embodiments", "one embodiment", "another embodiment" and the like mean "one or more (but not necessarily all) embodiments of the disclosed apparatus and/or method", unless expressly specified otherwise.

The term "determining" (and grammatical variants thereof) is used in an extremely broad sense. The term "determining" encompasses a wide variety of actions and therefore "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

The word "exemplary" or "example" is exclusively used herein to mean "serving as an example, instance, or illustration." Any embodiment described herein as "exemplary" or "example" is not necessarily to be construed as preferred or advantageous over other embodiments.

As used herein the terms "user" or "patient" or "subject" may be used interchangeably, and the foregoing terms comprise without limitation human beings, whether or not under the care of a physician, and other mammals. The terms "eye scan," "scanning the eye," or "scan the eyes," as used herein, are broad interchangeable terms that generally refer to the measurement of any part, substantially all, or all of the eye, including but not limited to the eye lens or any other tissue or nerve related to the eye.

The embedded computer subsystem can include at least one central processing unit (CPU) or "processor", memory, storage, a display and a communication link. An example of a CPU is the Intel Pentium microprocessor. The memory can be, for example, static random access memory (RAM) and/or dynamic random access memory. The storage can be accomplished with non-volatile RAM or a disk drive. A liquid crystal display is an example of the type of display that would be used in the device. The communication link can be a high speed serial link, an ethernet link or a wireless ("WiFi" or "broadband") communication link. The embedded computer subsystem can produce, for example, disease state predictions from collected data, perform calibration maintenance, perform calibration transfer, run instrument diagnostics, store a history of past analysis and other pertinent information, and in some embodiments, can communicate with remote hosts to send and receive data and new software updates. The communication link can be used for medical billing based on the number of test performed on each device. It can also be used for customer service to track failure or error rates on each device.

The embedded computer system can also contain a communication link that allows transfer of the subject's prediction records and the corresponding spectra to an external database. In addition, the communication link can be used to download new software to the embedded computer, update the multivariate calibration model, provide information to the subject to enhance the management of their disease, etc. The embedded computer system is very much like an information appliance. Examples of information appliances include personal digital assistants, web-enabled cellular phones and handheld computers. The communication link can be used for medical billing based on the number of test performed on each device. It can also be used for customer service to track failure or error rates on each device.

In a further example embodiment, a biomicroscope apparatus may be configured with, connected to or in communication with a system for automatically, remotely monitoring the operational status of one or more biomicroscopes disclosed herein each having a computer therein for determining device status information (e.g., usage counts, accounting/billing for usage, accounting/billing for usage over contract minimums, hardware or software error codes, storage or database operations to the point of failure for remote system diagnostics, capturing services response time until performance is restored, etc.) comprising an interference in the biomicroscope to intercept and pass status information from the computer to an interface for capturing and communicating the status information to a remote location, communication link between the interface for capturing and communicating information and the remote location, and a computer at the remote location to process the information. The system utilizes a scanner to poll the biomicroscope. The scanner, in cooperation with the central computer, can poll and monitor each of the biomicroscopes at a uniform rate or, when requested by the user at a central location, vary the poll rate of one or more of the biomicroscopes to poll the selected biomicroscope with increased regularity, slowing the polling rate of the other biomicroscopes, to provide a real-time monitoring of selected biomicroscopes. Depending on the results of a scan or poll sequence, the system may be configured to provide sound and voice capabilities so that the operator is afforded the option to communicate "live" with a customer service representative of a vendor or manufacturer of the biomicroscope to troubleshoot problems. The system is configured to utilize centralized computing and routing and or "cloud" computing or storage.

"Software" and "Machine-readable code operable on an electronic computer" are synonymous and refers to software or hard-wired instructions used to control the logic operations of the computer. The term computer or processor refers to an electronic computer or its specific logic-processing hardware. The machine-readable code is embodied in a tangible medium, such as a hard disc or hard-wired instructions.

The processor in the system may be a conventional microcomputer having keyboard and mouse input devices, a monitor screen output device, and a computer interface that operably connects various components of the system, for example, including an eye tracking assembly or device, robotic elements, etc.

It is to be further understood that all measurement values are approximate, and are provided for description. Although methods and materials similar or equivalent to those described herein can be used in the practice or testing of this disclosure, suitable methods and materials are described below. All publications, patent applications, patents, and other references mentioned herein are incorporated by reference in their entirety. In case of conflict, the present specification, including explanations of terms, will control. In addition, the materials, methods, and/or examples are illustrative only and not intended to be limiting.

Some features of the embodiments disclosed herein may be implemented as computer software, electronic hardware, or combinations of both. To illustrate this interchangeability of hardware and software, various components may be described generally in terms of their functionality. Whether such functionality is implemented as hardware or software depends upon the particular application and design constraints imposed on the overall system, as readily obtainable by a skilled person. Skilled persons may implement the described functionality in varying ways for each particular application, but such implementation decisions should not be interpreted as causing a departure from the scope of the claims.

Where a described functionality is implemented as computer software, such software may include any type of computer instruction or computer executable code or algorithm located or stored (even temporarily) within a memory device and/or transmitted as electronic signals over a system bus or network. Software that implements the functionality associated with components described herein may comprise a single instruction, or many instructions, and may be distributed over several different code segments, among different programs, and across several memory devices.

As used herein, "determining a disease state" includes determining the presence or likelihood of diabetes; the degree of progression of diabetes; a change in the presence, likelihood, or progression of diabetes; a probability of having, not having, developing, or not developing diabetes; the presence, absence, progression, or likelihood of complications from diabetes.

"Diabetes" includes a number of blood glucose regulation conditions, including Type I, Type II, and gestational diabetes, other types of diabetes as recognized by the American Diabetes Association (See ADA Committee Report, Diabetes Care, 2003) and similar governing bodies, hyperglycemia, impaired fasting glucose, impaired glucose tolerance, and pre-diabetes. Ocular tissue reflectance characteristic includes any reflectance property of tissue that is useful in correction of detected light found useful for estimating the tissue's intrinsic Fluorescence and Rayleigh scattering spectrum.

A "measure of chemical change due to glycemic control" means any change in the chemical characteristics of tissue that is due to glycemic control, examples including concentration, measurements of the presence, concentration, or change in concentration of glycation end-products in the ocular tissue; measurements of the rate or change in the rate of the accumulation of such end-products;

A "measure of glycation end-product" means any measure of the presence, time, extent, or state of ocular tissue associated with hyperglycemia, including, as examples, measurements of the presence, concentration, or change in concentration of glycation end-products in tissue; measurements of the rate or change in the rate of the accumulation of such end-products; measurements of the presence, intensity, or change in intensity of Fluorescence and the Rayleigh back scatter alone or in combination known to be associated with tissue glycation end-products; and measurements of the rate or change in the rate of the accumulation of such signal. When light is described as having a "single wavelength," it is understood that the light can actually comprise light at a plurality of wavelengths, but that a significant portion of the energy in the light is transmitted at a single wavelength or at a range of wavelengths near a single wavelength.

By way of example, there exist a number of non-invasive approaches for analyte concentration determination. These approaches vary widely, but have at least two common steps. First, an apparatus is used to acquire a reading from the body without obtaining a biological sample. Second, an algorithm converts this reading into an analyte (e.g., glucose) concentration estimation. One example of non-invasive analyte concentration analyzers includes those based upon the collection and analysis of spectra. Typically, a non-invasive apparatus uses some form of spectroscopy to acquire the signal or spectrum from the body. Spectroscopic techniques include but are not limited to Raman and fluorescence, as well as techniques using light from ultraviolet through the infrared [ultraviolet (200 to 400 nm), visible (400 to 700 nm), near-infrared (700 to 2500 nm or 14,286 to 4000 cm-1), and infrared (2500 to 14,285 nm or 4000 to 700 cm-1)]. A particular range for non-invasive analyte determination in diffuse reflectance mode is about 1100 to 2500 nm or ranges therein. It is important to note, that these techniques are distinct from the traditional invasive and alternative invasive techniques listed above in that the sample analyzed is a portion of the human body in-situ, not a biological sample acquired from the human body.

Three modes are generally used to collect non-invasive scans: transmittance, transflectance, and/or diffuse reflectance. For example the light, spectrum, or signal collected is light transmitted through a region of the body, diffusely transmitted, diffusely reflected, or transflected. Transflected refers to collection of the signal not at the incident point or area (diffuse reflectance), and not at the opposite side of the sample (transmittance), but rather at some point or region of the body between the transmitted and diffuse reflectance collection area. For example, transflected light enters the fingertip or forearm in one region and exits in another region. When using the near-infrared to sample skin tissue, the transflected radiation typically radially disperses 0.2 to 5 mm or more away from the incident photons depending on the wavelength used. For example, light that is strongly absorbed by the body, such as light near the water absorbance maxima at 1450 or 1950 nm, is collected after a small radial divergence in order to be detected and light that is less absorbed, such as light near water absorbance minima at 1300, 1600, or 2250 nm is, optionally, collected at greater radial or transflected distances from the incident photons.

The herein described example embodiments constitute an improvement of one or more of the methods and apparatuses (purportedly depicting the above-mentioned Accu-Chek D-Tector design) disclosed in the following patents, the entire disclosures (written description and drawings) of each are incorporated herein by reference:

U.S. Pat. No. 5,203,328 to Samuels entitled, "Apparatus And Methods For Quantitatively Measuring Molecular Changes In The Ocular Lens." This patent discloses an apparatus and method for determining whether a patient has diabetes. The system and method measure characteristics of the patient's eye that are indicative of diabetes. Specifically, the system and methods illuminate ocular tissue in a patient's eye, and measure backscattered light and fluorescent radiation generated by the ocular tissue in response to the excitation light. The intensity of the backscattered light and fluorescent light at particular wavelengths are then used to determine whether the patient has diabetes.

U.S. Pat. No. 5,582,168 entitled, "Apparatus And Methods For Measuring Characteristics Of Biological Tissues And Similar Materials." This patent exemplifies apparatuses and methods that combine two or more measurement techniques to arrive at a more accurate ultimate determination by measuring characteristics of biological tissues and similar materials. These apparatus and methods are described with respect to measurements of the human eye. In addition, the correction methodologies described therein involve measurements of elastically scattered excitation light. Samuels describes a simple linear correction technique.

U.S. Pat. No. 6,088,606 entitled, "Method and apparatus for determining a duration of a medical condition." This patent discloses a system and method for determining the duration of a medical condition and methods relating to determining the duration of a disease, not for diagnosing or screening for the presence of disease or for quantifying the concentration of specified chemical analytes.

U.S. Pat. No. 4,895,159 entitled, "Diabetes Detection Method," and U.S. Pat. No. 4,883,351 entitled, "Apparatus for the Detection of Diabetes and Other Abnormalities Affecting the Lens of the Eye," each disclose systems and methods for detecting the existence of diabetes using only backscattered light.

FIG. 1 shows a side-view of an eye 10. Eye 10 includes a cornea 11, an iris 12, a pupil 14, a lens 15, a retina 16 and optic nerve 17. Light enters the eye through pupil 14, is focused and inverted by cornea 11 and lens 15, and is projected onto retina 16 at the back of the eye. Iris 12 acts as a shutter that can be opened or closed to regulate the amount of light entering the eye via pupil 14.

The eye 10 consists of four quadrants in relation to the optic nerve head: (a) a temporal portion, which consists of the quadrant towards the temple of the skull, (b) a superior portion, which consists of the quadrant above the optic nerve head, (c) a nasal portion, which consists of the quadrant towards the nose, and (d) an inferior portion, which consists of the quadrant below the optic nerve head. In one aspect, measurements of a particular quadrant or quadrants of the ocular lens, i.e., temporal, superior, nasal, and/or inferior, can be collected/used to generate data on the structural features of the eye. In other words, in a example method for optical detection of AGE's in the lens of a subject's eye, the subject's eye may be exposed to a fixation point. Exposing the subject's eye to an excitation light source may comprise directing the light to a desired portion of the subject's eye. Directing the light to a desired portion of the subject's eye may comprise directing the light to a nasal portion, a temporal portion, a superior portion or an inferior portion of the lens. It may also comprise directing the light to other parts or tissues of the eye, such as, without limitation, the retina, the vitreous, the corona, etc.

In an example embodiment, an eye lens fluorescence biomicroscope is provided for use by ophthalmologists, optometrists and other healthcare professionals trained in routine eye exam, which is configured to aid in the diagnosis of diseases that affect the structural properties of the lens. The instrument comprises an optoelectronic unit and a computerized system of data acquisition and processing.

FIGS. 2 through 5A depict perspective, top and side views, respectively, of an example embodiment, for an example biomicroscope having an optical system, which comprises a blue LED illumination light source, confocal illumination and collector optics with an ability to scan a volume of measurement through the lens, analysis filters and detectors that measure both lens autofluorescence and scattered light from the sampling region. In addition, there is a red blinking LED target fixation light positioned within red blinking concentric rings to aid the patient in self-alignment, three IR LED lights to illuminate the eye, and a video camera. Specifically, the components of the optics unit include:

1. Biomicroscope light source
  a. Blue (e.g., 465 nm) LED excitation light
  b. Aperture
  c. Band pass filter (430-470 nm)
2. Biomicroscope focusing optics
  a. Source lens
  b. Collection lens with IR blocking filter
3. Biomicroscope light detector
  a. Silicon Photomultiplier with preamplifier, Peltier cooler, and power supplies.
  b. Front surface mirror.
  c. Stepper motor driven filter wheel with 25% neutral density, and long pass (500-1650 nm) filters.
4. Positioning optics
  a. Red blinking LED—fixation light, viewed within red blinking concentric rings provided by the lumen of a LED fixation tube (highlighted via darker lines in FIGS. 3 and 4.
  b. Three IR LED lights for camera illumination
  c. IR sensitive CCD video camera for positioning the pupil
5. A fluorescence reference target that can be positioned in the optical path during the self-test procedure at start up.

In an example embodiment, there is provided automatic tracking program for positioning the pupil of a patient's eye. The operator (e.g., health care professional or assistant) positions the subject's eye so that it is in focus on the computer screen and the system automatically aligns its optical axis before a measurement is taken. The operator knows the eye is being tracked the pupil tracker system because radial lines appear within the circle surrounding the pupil on the screen and a smaller circle appears within the pupil. The patient is instructed to close and open the eye (to wet the cornea with a tear film) to reduce blinking, and the operator clicks on the start icon to begin the scan. A blue LED light source is focused to achieve a converging excitation beam of blue light which is initially positioned just behind the posterior lens capsule. The collection optics are confocally aligned within a 1 mm diameter and 3 mm long volume of measurement that is scanned through. Below are Figures depicting example embodiments that show or identify various views and features discussed herein.

In an exemplary embodiment, the major functional components of are an optics unit and a laptop personal computer running any suitable operating system. The only components that contact a patient are shown in the perspective view figure below, namely a manually adjustable headrest (in/out) and a motorized adjustable chin rest (up/down). The motorized adjustable optics window (right/left motion) does not contact the patient.

In operation, an example embodiment is configured to project a focused beam of blue light on the lens of a patient and measures the autofluorescent green light from the lens non-invasively. To adjust the measurement for the effect of absorption of blue light by the lens, the example fluorescence biomicroscope is configured to measure scattered blue light and computes the ratio of autofluorescent to scattered light ("fluorescence ratio"). The clinician can compare the fluorescence ratio of a patient with the expected range of fluorescence ratios for the patient's age. By identifying patients with fluorescence ratios significantly higher than expected, a clinician can identify patients with signs of degenerative structural changes in the lens, identify potential risk of chronic systemic diseases in conjunction with the other data collected in a routine eye examination, and institute appropriate patient management plans.

In an exemplary system and method, the lens of the eye is illuminated with excitation light, and fluorescent emissions generated by the lens tissue in response to the excitation light are detected. Different characteristics of the fluorescent emissions, including the fluorescent emission intensity or the fluorescent lifetime may be determined. The determined characteristics of the detected fluorescent emissions are then compared to expected characteristics of the fluorescent emissions. The amount that the detected fluorescent characteristics deviate from the expected fluorescent characteristics is used to determine a duration that a patient has been experiencing a medical condition. In some instances, the backscattered portions of the excitation light may also be used to make the determination. Measuring the AGE intensity in a subject's eye lens may provide further benefits. For example, if multiple measurements are made over time, these measurements may be used to monitor the subject's response to dietary intervention strategies, nutritional supplementation, drugs, reduction of external oxidative stress factors such as smoking and/or other factors. Additionally, measuring the AGE intensity or severity of a subject's lens may provide a research tool for investigating correlations between AGEs and diseases in large subject populations.

In an example embodiment, a patient is positioned with its forehead centered on a headrest which is adjustable via a headrest knob. The patient's eye is illuminated by three near-infrared 880 nm LED lights and observed by an IR sensitive CCD video camera. An image of the eye is displayed on a computer screen to assist the operator in the alignment of the patient. The headrest is configured to be adjusted manually to bring the corneal plane of the patient eye close to an optics window so that the eye is in focus in the camera image visible on the computer screen. The patient is instructed to self-align by centering the red blinking LED fixation light with the surrounding red blinking concentric rings. Using a computer interface, the operator can adjust a chin rest vertical position and horizontal position of the optics window to enable the patient to sit comfortably with the fixation target properly positioned. The operator adjusts the optics window and chin rest by clicking arrow icons on the computer screen, which control stepper motors.

In a further exemplary embodiment, the optical path is aligned with the eye of the subject by moving a chin rest, headrest, and the optical axis until the target is centered in the pupil and the iris is brought into focus. The appropriate focus is determined by an IR camera viewed by an operator (health care worker). The patient fixates on a target to ensure stability of the eye and relaxation of accommodation. The target remains visible during the scan.

The computer is configured to include software to control an automatic tracking program for positioning the pupil. The operator positions the patient's eye so that it is in focus on the screen and the system automatically aligns its optical axis before a measurement is taken. As the patient eye is tracked, radial lines appear within an alignment circle surrounding the pupil on the computer screen and a smaller circle appears within the pupil. The patient is then instructed to close and open the eye (to wet the cornea with a tear film) to reduce blinking, and the operator clicks on the start icon to begin the scan. A blue LED light source is focused to achieve a converging excitation beam of blue light, which is initially positioned just behind the posterior lens capsule. Collection optics are confocally aligned within a 1 mm diameter and 3 mm long volume of measurement that is scanned through the lens in 0.31 mm steps. In the eye, blue light is scattered by elastic (Rayleigh scattering) and inelastic (fluorescent) interactions with lens proteins (such as AGEs).

In the detection path, a filter rejects red and infrared light from the positioning infrared LED. A rotating filter wheel alternately chops the beam into blue and green (primarily Rayleigh scattered) and green (fluorescent) segments. The alternating scattered and fluorescent light is focused on a highly sensitive silicon photomultiplier and the signals are sent to the A/D converter on the optics control board and then to the computer.

Under software control, the volume of measurement at the focal points of the light source and detector is scanned from just behind the posterior lens capsule, through the lens, through the anterior lens capsule to the aqueous humor, and then back again. Computer software records both scattered and fluorescent light during the forward and reverse scan and constructs a graph of each that is displayed on the computer monitor. Software detects the front and back surfaces of the lens capsule on the graph, estimates the apparent thickness of the lens, and computes the average of the ratio of lens autofluorescence to scattered light in the central portion of the lens. The software checks that the apparent lens thickness is within a physiological range. Software also detects anomalies in the scan, such as eye blinks, which could cause an inaccurate measurement, or excessive difference between the two scans. For valid scans, the fluorescence ratio is reported; otherwise, for anomalous scans, an error code is reported on the computer monitor and the fluorescence ratio is not reported. In the case of an error code, the clinician can then re-scan the eye. If the scan is valid, the software program produces a report that is displayed on the screen and that can be printed for the patient and/or for the patient's file. The scan data is also automatically saved on the computer's hard disk.

In this example embodiment, there is an advantageous fixation target system configuration that addresses another drawback of the Accu-Chek D-Tector, namely that during use, patients are seated and asked to position their forehead on a stationary head rest provided and to look at a visual fixation target located therein. Insofar as patient/system interaction is concerned, any voluntary or involuntary movement of the patient's eye during treatment can significantly alter the alignment of the eye relative to the accuracy of the detection. It is necessary, therefore, for the patient to his eye stationary during the test. The purpose of the fixation target system is to assure that the patient is looking along a desired line of sight within narrow limits and to assure that the location of the eye when viewed by the instrument camera is well defined. This is done by presenting a visual fixation target to the patient such that the patient's eye is rotated superiorly and nasally at desired angles. The visual fixation target encourages the patient to fixate on the target. The optical axis of the patient's line of sight is displaced about 15 degrees up and about 15 degrees inward to avoid specular reflections from the eye to affect the fluorescence measurement.

At first, the target may not be visible to the patient because the optical axis is not sufficiently aligned to the eye. The operator, while viewing the patient's eye displayed on the computer screen, brings the viewing and illumination optics into the central region of the eye by adjusting the push-button controls on the computer screen. In the Accu-Chek D-Tector, the patient fixates on a 0.5 mm dia. red LED target located at a distance of about 150 mm, which is viewed through a 4 mm dia. aperture. Patients typically have trouble locating the aperture and the LED target because of the accuracy of the narrow angle required to even see the LED target because the patient is essentially being asked to look at the LED target through a straw when he can't even see the near end of the straw and no visual cues as to where to move his head and where to look to achieve alignment. The anterior and posterior capsule boundaries are automatically noted as the eye is scanned along the visual axis of the lens. Having located the positions of the front and rear of the lens the system then scans along the visual axis of the lens selecting points from which fluorescence data are recorded.

In another example embodiment, which may provide a more accurate measurement result, the intensity of the fluorescent light is normalized, using backscattered excitation light, to account for a variety of factors. Such factors could include variations in the opacity of the target tissue, which can vary with a patient's age or physical condition. In such a system, a detector would be capable of determining an intensity of the fluorescent light generated by the target tissue, as well as an intensity of excitation light that is backscattered from a patient's eye. Because the fluorescent light will usually have a different wavelength than the backscattered excitation radiation, the detector can be configured to detect the intensity of light returned from the target tissue at the different respective wavelengths for the excitation light and the fluorescent light. A ratio of the fluorescent light intensity to the intensity of the backscattered excitation light is then determined, thereby normalizing the peak intensity of the fluorescent component. The normalized fluorescent intensity is then compared to an expected normalized fluorescent intensity to determine a duration that the patient has been experiencing a medical condition.

Variations in the opacity or transmissivity of the target tissue (e.g., lens of a patient's eye) can affect the amount of excitation light that is actually delivered to the target tissue, and the amount of fluorescent light that escapes the target tissue and is detected by the detector. Normalizing the fluorescent light with the backscattered light creates a measure of the fluorescent light that automatically accounts for variations in the amount of excitation light energy actually delivered to the target tissue, and variations in the amount of fluorescent light that escapes the patient's eye after the fluorescent light is generated. In a particular example embodiment, where the intensity of fluorescent light returned from the target tissue is normalized, the Rayleigh component of the backscattered excitation light is used for the normalization.

Alternatively, a simpler embodiment may be constructed that is configured to measure the fluorescence component alone and not measure or normalize to the back scattered signal, thereby eliminating the need for a filter wheel. Fluctuations in the intensity of the LED over time for this configuration may require a reference detector or calibration target within the device. Fluorescence can be measured at a specific time/delay after the excitation pulse (typically 1-10 ns) which eliminates the need for a band pass filter, just a delay on the detector measurement. Further, a Dichroic beam splitter arrangement can be used in place of the filter wheel to separate the fluorescence and scatter signals for measurement on separate detectors and thereby save space.

An aperture can be used on the excitation and collection optics to control the size of the sample volume created within the human lens. The sample volume should be maximized to increase the number of photons and SNR of the measurement, but should be no larger than the human lens (3-5 mm thick).

The need for motion control for tracking of the pupil can be eliminated by a handheld configuration that is stabilized on the subject by use of a suitable means, such as an eyecup or forehead rest. In use, an operator manually positions a video target on the pupil. The optics elements would be configured to continually or singly scan through the human lens using a mechanical oscillator (e.g., voice coil, piezo, motion stage), and there providing a capability to analyze each scan and alerting the operator when a successful scan is captured. An excitation, collection and video axis can be combined to share a common lens, which can more easily be scanned.

In a further embodiment, an array of LED and detector pairs can be configured to form an array of sample volumes so no mechanical movement is needed for scanning sample volumes. Optimal sample volumes can thereby be selected from a given LED/detector pair.

Further, it would desirable to have a portable, handheld, robust, cost-effective, non-invasive and rapid imaging-based method or device configured for detection of a fluorescence signal with Rayleigh or Raman scattering from a "volume of measurement" where, for example, confocal beams of light intersect for objectively assessing ocular tissues. Such a method or device would detect changes at the biological, biochemical and cellular levels for rapidly, sensitively and non-invasively detecting or diagnosing the earliest presence of pre-diabetic conditions. Such a portable method, device or instrument as described herein would have commercial potential.

Having determined which wavelength to use for the source and which portion of the recorded spectrum to examine to measure the fluorescent response, it is possible to design a much simpler, dedicated system, capable of making the same measurement. This would be accomplished by using custom optics to both deliver and collect the light, one achieves a direct optical path through, for example, a suitable configuration of optical filters and dichroic beam splitters to discrete photo-detectors. In comparison to the fiber coupled spectrometer and diode array, optical efficiency may be increased by several orders of magnitude.

In a further exemplary embodiment, a portable (handheld) device may generally comprise the following features: (i) one or more excitation/illumination light sources and (ii) a detector device (e.g., a digital imaging detector device, or (detection of a fluorescence signal with Rayleigh or Raman scattering from a "volume of measurement" where confocal beams intersect) which may be combined with one or more optical emission filters, or spectral filtering mechanisms, and which may have a view/control screen (e.g., a touch-sensitive screen), image capture and zoom controls. The device may also have: (iii) a wired and/or wireless data transfer port/module, (iv) an electrical power source and power/control switches, and/or (v) an enclosure, which may be compact and/or light weight, and which may have a mechanism for attachment of the detector device and/or a handle grip. With an on board battery and rechargeable AC/DC thru a wire or non-wire proximal connected charger base unit. The excitation/illumination light sources may be LED arrays emitting light at any suitable wavelength(s) (as described above), such as, without limitation, at about 430 to about 470 nm, and may be coupled with additional band-pass filters to remove/minimize the side spectral bands of light from the LED array output so as not to cause light leakage into the imaging detector with its own optical filters. The digital imaging detector device may be a digital camera, for example having at least an ISO800 sensitivity, but more preferably an ISO3200 sensitivity, and may be combined with one or more optical emission filters, or other equally effective (e.g., miniaturized) mechanized spectral filtering mechanisms (e.g., acousto-optical tunable filter or liquid crystal tunable filter). The digital imaging detector device may have a touch-sensitive viewing and/or control screen, image capture and zoom controls. The enclosure may be an outer hard plastic or polymer shell, enclosing the digital imaging detector device, with buttons such that all necessary device controls may be accessed easily and manipulated by the user. Miniature heat sinks or small mechanical fans, or other heat dissipating devices may be imbedded in the device to allow excess heat to be removed from the excitation light sources if required. The complete device, including all its accessories and attachments, may be powered using standard AC/DC power and/or by rechargeable battery pack. The complete device may also be attached or mounted to an external mechanical apparatus (e.g., tripod, or movable stand with pivoting arm) allowing mobility of the device within a clinical room with hands-free operation of the device. Alternatively, the device may be provided with a mobile frame such that it is portable. The device may be cleaned using moist gauze wet with water, while the handle may be cleansed with moist gauze wet with alcohol and be composed of any suitable anti-bacterial hard plastic. The device may include software allowing a user to control the device, including control of imaging parameters, visualization of images and fluorescence and Rayleigh scatter as one objective value, storage of image data or measured value and user information, transfer of images and/or associated data, and/or relevant image analysis (e.g., diagnostic algorithms) and detection of a fluorescence signal with Rayleigh or Raman scattering from a "volume of measurement" where the confocal beams intersect.

With an increase in detection efficiency, source intensity may be correspondingly lowered by employing a low power, short arc lamp, with appropriate optics and an optical filter can provide enough optical power. Other suitable sources include laser diodes coupled to frequency doubling device, blue LEDs and filtered, special purpose incandescent lamps. To exclude specular reflections from the detectors, polarization filters are proposed for both transmit and receive optics. In addition, the electronics associated with the detection and processing comprise two analog preamps used with the detectors, and a single chip microcontroller equipped with onboard analog to digital (A/D) conversion. Embedded firmware would direct the operator through a measurement event and then either display the processed measurement information on the systems own digital display, or log this data to a computer via a serial interface, for example.

A device and method for fluorescence-based monitoring is disclosed, in some aspects, the device comprises an optical (e.g., fluorescence and/or reflectance) device for real-time, non-invasive imaging of biochemical and/or organic substances. This device may be compact, portable, and/or hand-held, and may provide high-resolution and/or high-contrast images. This imaging device may rapidly and conveniently provide the clinician/health care worker with valuable biological information of the ocular region. The device may also facilitate image-guided collection of swab/biopsy samples, imaging of exogenous molecular biomarker-targeted and activated optical (e.g., absorption, scattering, fluorescence, reflectance) Also capable of detecting fluorescent marked therapeutic agents to measure drug interactions and therapeutic compliance, contrast agents either in vivo or ex vivo. and may permit longitudinal monitoring of therapeutic response for adaptive intervention in diabetes management. By exploiting wireless capabilities with dedicated image analysis and diagnostic algorithms, the device may be integrated seamlessly into telemedicine (e.g., E-health) infrastructure for remote-access to specialists in health care. Such a device may also have applications outside diabetes or eye care, including early detection of cancers, monitoring of emerging photodynamic therapies, detection and monitoring of stem cells, and as an instrument in the dermatology and cosmetology clinics, in addition to other applications.

In some aspects, there is provided a device for fluorescence-based imaging and detection of a fluorescence signal with Rayleigh or Raman scattering from a "volume of measurement" where confocal beams intersect and monitoring of a target comprising: a light source emitting light for illuminating the target, the emitted light including at least one wavelength or wavelength band causing at least one biomarker associated with the target to fluoresce; and a light detector for detecting the fluorescence. In other aspects, there is provided a kit for fluorescence-based imaging and monitoring of a target comprising: the device as described above; and a fluorescing contrast agent for labeling the biomarker at the target with a fluorescent wavelength or wavelength band detectable by the device. In still other aspects, there is provided a method for fluorescence-based imaging and monitoring a target comprising: illuminating the target with a light source emitting light of at least one wavelength or wavelength band causing at least one biomarker to fluoresce; and detecting fluorescence of the at least one biomarker with an image detector.

One example embodiment of the apparatus is a portable optical digital imaging device. The device may utilize a combination of white light, ocular tissue fluorescence and reflectance imaging, and may provide real-time assessment, recording/documenting, monitoring and/or care management. The device may be hand-held, compact and/or lightweight. This device and method may be suitable for monitoring of ocular tissues in humans and animals. Without limitation, the device may include a power supply such as an AC/DC power supply, a compact battery bank, or a rechargeable battery pack. Alternatively, the device may be adapted for connecting to an external power supply. The device may be hardened or contain suitable shock absorbing features for drop and shock wear and tear experienced for military field applications.

All components of the exemplary digital imaging and detection of a fluorescence signal with Rayleigh or Raman scattering from a "volume of measurement" where the confocal beams intersect device may be integrated into a single structure, such as an ergonomically designed enclosed structure with a handle, allowing it to be comfortably held with one or both hands. The device may also be provided without any handle. The device may be lightweight, portable, and may enable real-time digital imaging and detection of a fluorescence signal with Rayleigh or Raman scattering from a "volume of measurement" where the confocal beams intersect (e.g., still and/or video) of any target surface using blue or white light, fluorescence and/or reflectance imaging modes.

The device may be scanned across the eye tissue surface for imaging by holding it at variable distances from the surface, and may be used in a lit environment/room to image white or blue light reflectance/fluorescence. The device may be used in a dim or dark environment/room to optimize the tissue fluorescence signals, and minimize background signals from ambient lights. The device may be used for direct (e.g., with the unaided eye) or indirect (e.g., via the viewing screen of the digital imaging device) visualization of ocular tissues (e.g., lens of the eye) and surrounding tissues (e.g., retina, vitreous, etc.). The device may have a suitable housing that houses all the components in one entity or as a modular unit intergrated into another device like a surgical microscope or auto refractor. The housing may be equipped with a means of securing any digital imaging device within it. The housing may be designed to be hand-held, compact, and/or portable. The housing may be one or more enclosures.

An example of a handheld portable device for fluorescence-based monitoring is described below. All examples are provided for the purpose of illustration only and are not intended to be limiting. Parameters such as wavelengths, dimensions, and incubation time described in the examples may be approximate and are provided as examples only.

In this exemplary embodiment, the device uses two violet/blue light (e.g., 430-470 nm run +/−10 run emission, narrow emission spectrum) LED arrays, each situated on either side of the imaging detector assembly as the excitation or illumination light sources. These arrays have an output power of approximately 1 Watt each, emanating from a 2.5×2.5 cm2, with a 70-degree illuminating beam angle. The LED arrays may be used to illuminate the ocular tissue surface from a distance of about 10 cm, which means that the total optical power density on the tissue surface is about 0.08 W/cm2. At such low powers, there is no known potential harm to the eyes from the excitation light.

The one or more light sources may be articulated (e.g., manually) to vary the illumination angle and spot size on the imaged surface, for example by using a built in pivot, and are powered for example through an electrical connection to a wall outlet and/or a separate portable rechargeable battery pack. Excitation/illumination light may be produced by sources including, but not limited to, individual or multiple light-emitting diodes (LEDs) in any arrangement including in ring or array formats, wavelength-filtered light bulbs, or lasers. Selected single and multiple excitation/illumination light sources with specific wavelength characteristics in the ultraviolet (UV), visible (VIS), far-red, near infrared (NIR) and infrared (IR) ranges may also be used, and may be composed of a LED array, organic LED, laser diode, or filtered lights arranged in a variety of geometries. Excitation/illumination light sources may be 'tuned' to allow the light intensity emanating from the device to be adjusted while imaging. The light intensity may be variable. The LED arrays may be attached to individual cooling fans or heat sinks to dissipate heat produced during their operation. The LED arrays may emit any suitable wavelength or wavelengths of light, which may be spectrally filtered using any suitable commercially available band-pass filter (Chroma Technology Corp, Rockingham, Vt., USA) to reduce potential 'leakage' of emitted light into the detector optics. When the device is held adjacent to ocular tissue to be imaged, the illuminating light sources may shine a narrow-bandwidth or broad-bandwidth violet/blue wavelength or other wavelength or wavelength band of light onto the ocular tissue surface thereby producing a flat and homogeneous field within the region-of-interest. The light may also illuminate or excite the tissue down to a certain shallow depth. This excitation/illumination light interacts with the normal and diseased tissues and may cause an optical signal (e.g., absorption, fluorescence and/or reflectance) to be generated within the tissue.

By changing the excitation and emission wavelengths accordingly, the imaging device may interrogate ocular tissue components (e.g., lens, retina, etc.) at the surface and at certain depths within the observed eye tissue strucures. For example, by changing from violet/blue (−400-500 nm ran) to green (−500-540 nm ran) wavelength light, excitation of deeper tissue fluorescent sources may be achieved. Similarly, by detecting longer wavelengths, fluorescence emission may be detected. For medical condition assessment, the ability to interrogate ocular tissue surface fluorescence may be useful, for example in detection and potential identification of pre-diabetes.

In a further example embodiment, the device may be used with any standard compact digital imaging device (e.g., a charge-coupled device (CCD) or complementary metal-oxide-semiconductor (CMOS) sensors) as the image acquisition device. The example device shown in a) has an external electrical power source, the two LED arrays for illuminating the object/surface to be imaged, and a commercially available digital camera with stabilized optics for target acquisition negating an operators slight movements securely fixed to light-weight metal frame equipped with a convenient handle for imaging. A multi-band filter is held in front of the digital camera to allow wavelength filtering of the detected optical signal emanating from the object/surface being imaged. The camera's video/USB output cables allow transfer of imaging data to a computer for storage and subsequent analysis. This example embodiment uses a commercially-available 8.1-megapixel Sony digital camera (Sony Cybershot DSC-T200 Digital Camera, Sony Corporation, North America). This camera may be suitable because of i) its slim vertical design which may be easily integrated into the enclosure frame, ii) its large 3.5-inch widescreen touch-panel LCD for ease of control, iii) its Carl Zeiss 5× optical zoom lens, and iv) its use in low light (e.g., ISO 3200). The device may have a built-in flash which allows for standard white light imaging (e.g., high-definition still or video with sound recording output). Camera interface ports may support both wired (e.g., USB) or wireless (e.g., Bluetooth, WiFi, and similar modalities) data transfer or 3rd party add-on modules to a variety of external devices, such as: a head-mounted display, an external printer, a tablet computer, laptop computer, personal desk top computer, a wireless device to permit transfer of imaging data to a remote site/other device, a global positioning system (GPS) device, a device allowing the use of extra memory, and a microphone. The digital camera is powered by rechargeable batteries, or AC/DC powered supply. The digital imaging device may include, but is not limited to, digital cameras, webcams, digital SLR cameras, camcorders/video recorders, cellular telephones with embedded digital cameras, Smartphones™, personal digital assistants (PDAs), and laptop computers/tablet PCs, or personal desk-top computers, all of which contain/or are connected to a digital imaging detector/sensor.

This light signal produced by the excitation/illumination light sources may be detected by the imaging device using optical filter(s) (e.g., those available from Chroma Technology Corp, Rockingham, Vt., USA) that reject the excitation light but allow selected wavelengths of emitted light from the tissue to be detected, thus forming an image or signal in the form of a fluorescence signal or trace on the display. There is an optical filter holder attached to the enclosure frame in from of the digital camera lens which may accommodate one or more optical filters with different discrete spectral bandwidths. These band-pass filters may be selected and aligned in front of the digital camera lens to selectively detect specific optical signals from the ocular tissue surface based on the wavelength of light desired. Spectral filtering of the detected optical signal (e.g., absorption, fluorescence, and reflectance) may also be achieved, for example, using a liquid crystal tunable filter (LCTF), or an acousto-optic tunable filter (AOTF) which is a solid-state electronically tunable spectral band-pass filter. Spectral filtering may also involve the use of continuous variable filters, and/or manual band-pass optical filters. These devices may be placed in front of the imaging detector to produce multispectral, hyperspectral, and/or wavelength-selective imaging of tissues.

The device may be modified by using optical or variably oriented polarization filters (e.g., linear or circular combined with the use of optical wave plates) attached in a reasonable manner to the excitation/illumination light sources and the imaging detector device. In this way, the device may be used to image the tissue surface with polarized light illumination and non-polarized light detection or vice versa, or polarized light illumination and polarized light detection, with either white light reflectance and/or fluorescence imaging. This may permit imaging with minimized specular reflections (e.g., glare from white light imaging), as well as enable imaging of fluorescence polarization and/or anisotropy-dependent changes in ocular tissues.

In an example embodiment, the device may also be embodied as not being hand-held or portable, for example as being attached to a mounting mechanism (e.g., a tripod or stand) for use as a relatively stationary optical imaging device for white light, fluorescence and reflectance imaging of objects, materials, and surfaces (e.g., an eye). This may allow the device to be used on a desk or table or for 'assembly line' imaging of objects, materials and surfaces. In some embodiments, the mounting mechanism may be mobile.

Other features of this device may include the capability of digital image and video recording, possibly with audio, methods for documentation (e.g., with image storage and analysis software), and wired or wireless data transmission for remote telemedicine/E-health needs. For example, an embodiment of the device is configured to include a mobile communication device such as a cellular telephone. The cellular telephone used in this example is a Samsung Model A-900, which is equipped with a 1.3 megapixel digital camera. The telephone is fitted into the holding frame for convenient imaging. The images from the cellular telephone may be sent wirelessly to another cellular telephone, or wirelessly (e.g., via Bluetooth connectivity) to a personal computer for image storage and analysis. This demonstrates the capability of the device to perform real-time hand-held fluorescence imaging and wireless transmission to a remote site/person as part of a telemedicine/E-health diabetes care infrastructure. In order to demonstrate the capabilities of the imaging device in health care and other relevant applications, a number of feasibility experiments are conducted using the particular example described. It should be noted that during all fluorescence imaging experiments, the Sony camera (Sony Cybershot DSC-T200 Digital Camera, Sony Corporation, North America) settings are set so that images are captured without a flash, and with the 'Macro' imaging mode set. Images are captured at 8 megapixels. The flash was used to capture white light reflectance images. All images are stored on the xD memory card for subsequent transfer to a personal computer for long-term storage and image analysis. All white light reflectance and fluorescence images/movies captured with the device are imported into Adobe Photoshop for image analysis. However, image analysis software was designed using MatLab™ (Mathworks) to allow a variety of image-based spectral algorithms (e.g., red-to-green fluorescence ratios, etc) to be used to extract pertinent image data (e.g., spatial and spectral data) for quantitative detection/diagnostic value. Image post-processing also included mathematical manipulation of the images.

Figure 6:
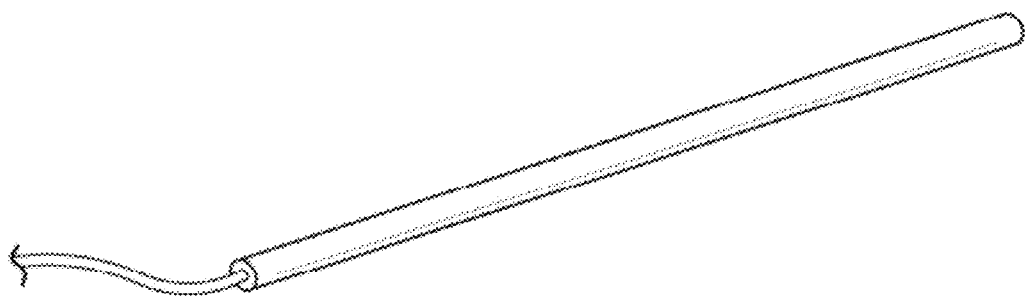
FIGS. 6 and 6A depict perspective views of an example embodiment of an improved fixation target system.
Figure 6A:
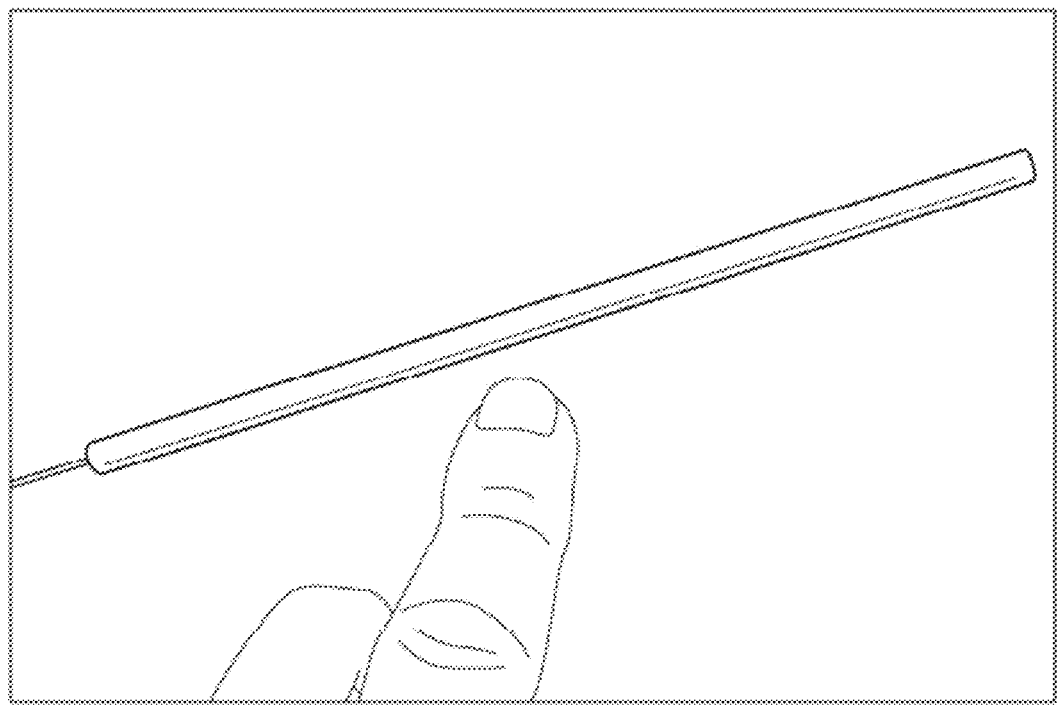

Still further, there is provided an improved fixation target system that advantageously employs visual cues via an alignment tube to help a patient self-align and locate the aperture in order to help a patient more readily determine where to move his head and/or eye (gaze) to achieve alignment with an LED fixation target, which may or may not be blinking. In one aspect, the alignment tube comprises a cylinder whose inner lumen surface is shiny or highly reflective along its length. Centered at the far end of the cylindrical tube is an LED assembly. For example, suitable cylinders are metal or may be plastic or any other material so long as the inner lumen is a shiny and highly reflective cylindrical surface. See FIG. 6 (photograph) and 6A (schematic) showing an example embodiment comprising a metallic tube having an LED and aperture embedded in the end of the tube with its wire lead showing.

Figure 7:
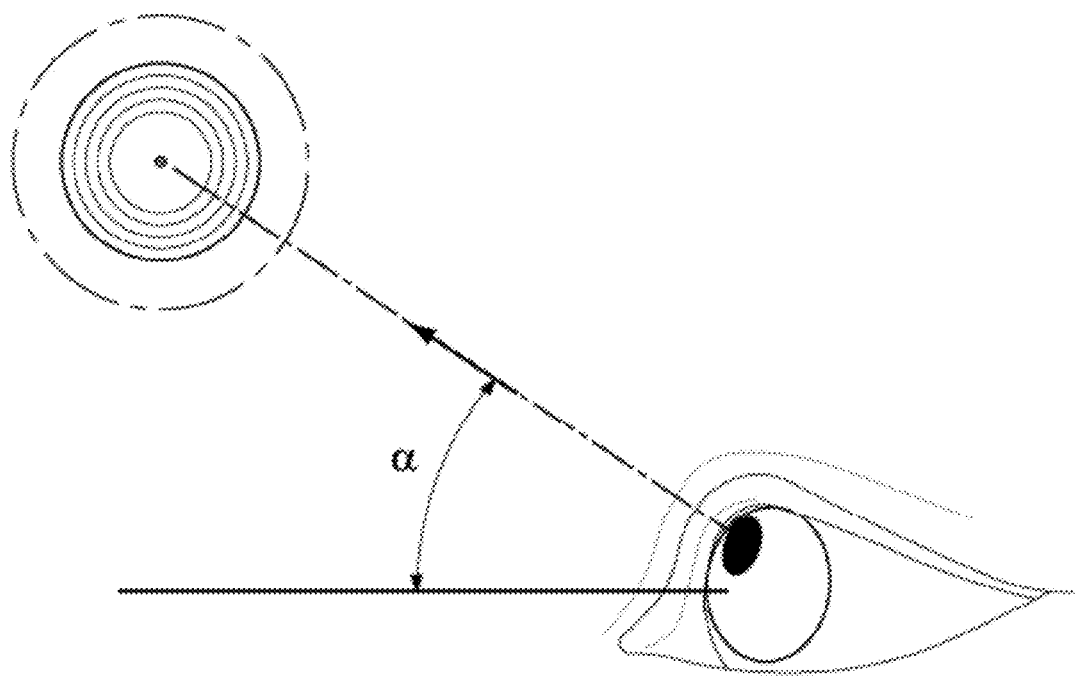
FIGS. 7 and 7A depict schematic and photographic views, respectively, of an example embodiment of an improved fixation target system as viewed by a patient.
Figure 7A:
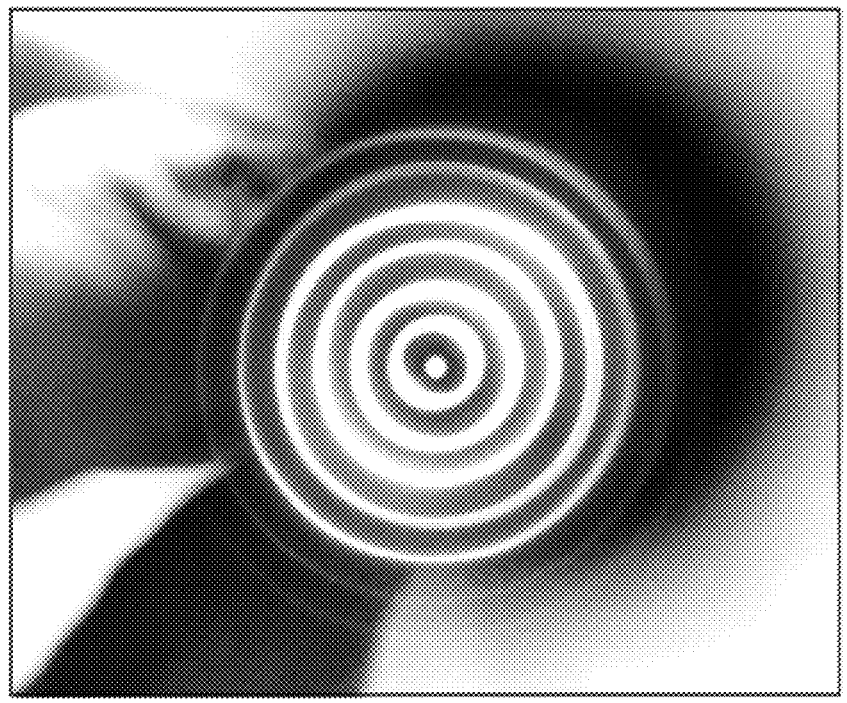
Figure 8:
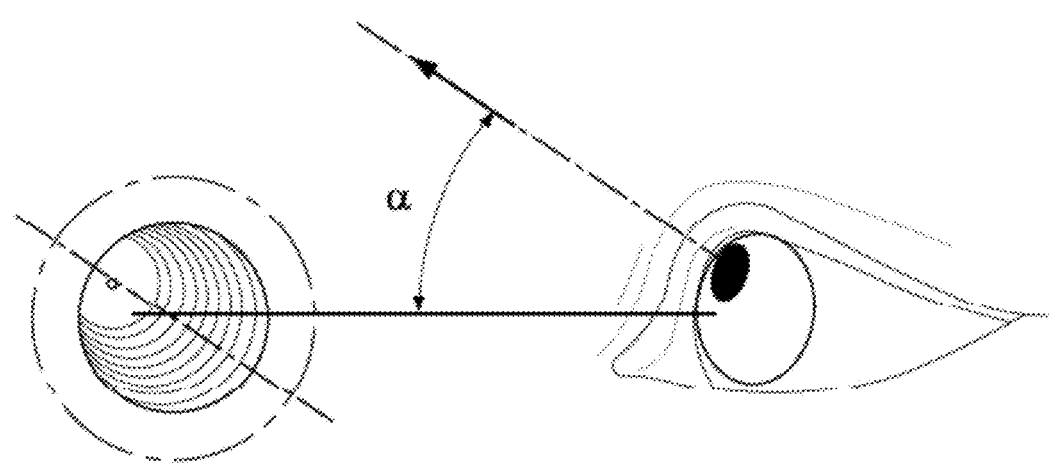
FIGS. 8 and 8A depict schematic and photographic views, respectively, of an example embodiment of an improved fixation target system as viewed by a patient.
Figure 8A:
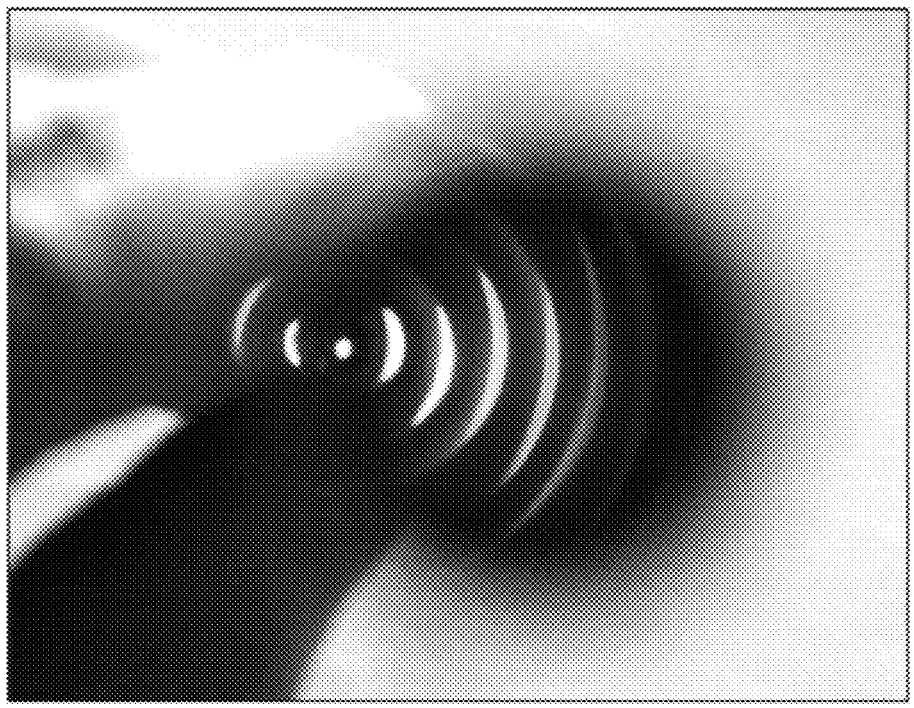

This enables the patient to see the inner wall of the LED-illuminated tube from a fairly large angle so that he can readily see the tube entrance and attempt to align his view by moving his head to center a set of nested circles formed by the multiple reflected images of the LED. When viewed by the patient with his line of sight along the axis of the tube, the nested circles will appear to be concentric and centered on the LED. See FIG. 7 (schematic) and 7A (photograph). If the patient's view is misaligned, i.e., not exactly along the center axis of the lumen of the tube, the circles will appear to be non-concentric (i.e., skewed off axis) and the LED target may not be directly visible. See FIG. 8 (schematic) and 8A (photograph). The patient can then self-align by making body, head or eye adjustments to center LED within the reflected circles and finally center the LED target along, for example, the center axis of the LED fixation alignment tube.

Figure 9:
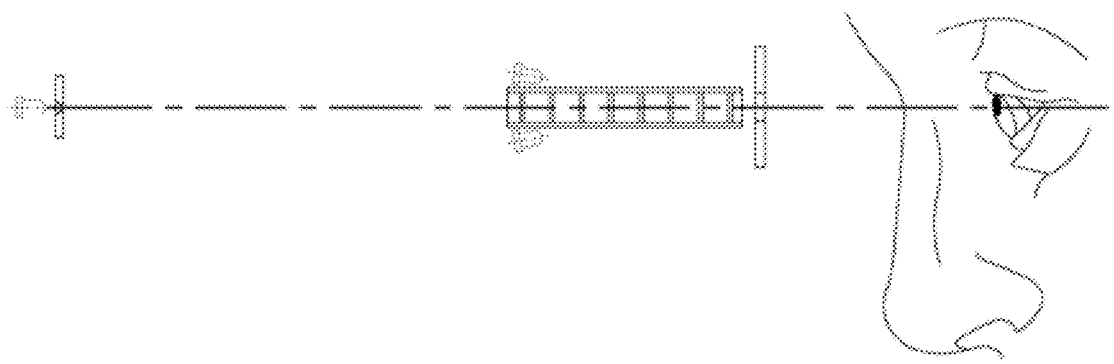
FIG. 9 depicts a schematic side view of an example embodiment of an improved fixation target system being viewed by a patient.

In a further example embodiment, the LED fixation alignment tube may be translucent, and back-lighted by a different color light source with a series of alternating opaque and clear annular rings along its length. The patient's view will be similar to the above description with eccentric rings being seen when the line of sight is misaligned. See FIG. 9 depicting a patient's view centered along the optic axis of a schematic of this example embodiment.

In other embodiments, a fixation point such as a blinking LED may be used without a tube, as described above, to position the subject's eye in order to align the subject's eye such that an exact inferior location is presented to which the excitation light is directed. The fixation point is provided by an LED of any suitable color, may include a fixation target of one or more multiple fixation points in a cross-hairs configuration to facilitate fixation of a subject's eye. In an alternative embodiment, it is envisioned that the fixation point may be in optical communication with a beam splitter positioned at a suitable angle of incidence in relation to the subject's eye and may reflect the fixation point into the subject's eye. In a computer automated system the subject's eye must be fixated before the excitation light is directed into the subject's eye and sample volumes are collected.

Other example embodiments comprise an apparatus and method suitable for determining properties of in vivo tissue from spectral information collected from the lens of the eye. An illumination light system provides excitation light at one or more wavelength ranges, which are communicated to an optical collection device (e.g., photodetector). Light homogenizers and mode scramblers can be employed to improve the performance in some embodiments. The optical system is non-invasive and does not physically contact or intrude the eye or skin. The optical source essentially receives light from the illumination system and transmits it to the lens of the eye. The optical collection system and/or device receive(s) light emitted from the eye lens tissue by fluorescence thereof in response to the excitation light. The optical collection system can communicate the light to a spectrograph which produces a signal representative of the spectral properties of the light. An analysis system (computer) determines a property of the eye lens from the spectral properties.

In a further example embodiment, a method for determining a measure of a tissue or disease state (e.g., glycation end-product or disease state) in an individual is provided. A portion of the tissue of the individual is illuminated with excitation light, then light emitted by the tissue due to fluorescence of a chemical in the tissue responsive to the excitation light is detected. The detected light can be combined with a model relating fluorescence with a measure of tissue state to determine a tissue state. The embodiments can comprise single wavelength excitation light, scanning of excitation light (illuminating the tissue at a plurality of wavelengths), detection at a single wavelength, scanning of detection wavelengths (detecting emitted light at a plurality of wavelengths), and combinations thereof. The example embodiment also can comprise correction techniques that reduce determination errors due to detection of light other than that from fluorescence of a chemical in the tissue. For example, the reflectance of the tissue can lead to errors if appropriate correction is not employed. The embodiment can also comprise a variety of models relating fluorescence to a measure of tissue state, including a variety of methods for generating such models. Other biologic information can be used in combination with the fluorescence properties to aid in the determination of a measure of tissue state. The embodiment also comprises apparatuses suitable for carrying out the method, including appropriate light sources, detectors, and models (for example, implemented on computers) used to relate detected fluorescence and a measure of tissue state.

Some example embodiments provide techniques for measuring light scattering within a subject's eye, e.g., a human eye, for diagnostic purposes. For example, a light scattering system includes an excitation light assembly that shines a light (e.g., LED or laser beam) into a subject's eye. A transfer lens focuses the scattered laser light forming an image on a measurement mirror. Between the transfer lens and the measurement mirror the light is reflected from a steerable mirror that can be adjusted to position the image on the measurement mirror at a desired position. The measurement mirror has a pinhole that allows some of the scattered laser light to pass through and be detected by a single photon detector and analyzed by a hardware or software correlator. The scattered laser light not passing through the pinhole is reflected by the measurement mirror toward a charge-coupled device (CCD) camera. The camera obtains images of the scattered laser light and provides the images to a computer. The computer obtains information from the correlator and the images from the camera. The computer can analyze the output of the correlator (the correlation function) relating measured scattered light and position within the eye to determine whether the eye has indications of abnormalities such as diseases. The computer can further process the image information from the camera to provide images of the scattered light from the eye and to send control signals to the steering mirror to adjust for movement of the subject's eye and to help insure that light from a desired location of the eye is being directed through the pinhole of the measurement mirror. This light scattering system is exemplary, however, and not limiting as other implementations in accordance with the disclosure are possible.

In a further example embodiment, an excitation light source (e.g., blue LED) may be used to illuminate a specific point in the lens of a subject's eye that is approximately 50% to 80% (optionally, 60% to 75%) and all subranges therebetween, from the front edge of the inferior quadrant of the subject's lens. It has been determined that measurements at this location in the mammalian eye provide consistent measurements without undesirable delays or interference that can skew data collection. For example, care should be taken in fluorescence spectroscopy to avoid confounding influences of unwanted optical signals in the detection of the compound of interest (e.g., AGEs). There may be potentially confounding influences from macular pigments, cataracts, fluorescence emissions from areas other than the lens, etc. The influence from these and other factors may be reduced by choosing an excitation wavelength that is just outside the absorption of the undesirable influence but still overlapping the AGEs absorption on its long-wavelength shoulder, in the green wavelength region. As such, measurements taken from inferior position, as mentioned above, are advantageous because interferences are minimized.

In an example embodiment, the returned light can include fluorescent light generated by the AGEs in the lens of the eye. The intensity of the returned fluorescent light can be compared to a chronologically age-related expected intensity of fluorescent light for individuals that do not have diabetes. Optionally, an amount that the intensity of the actual returned fluorescent light exceeds an expected intensity for returned fluorescent light can then be used to determine a duration and/or severity that the individual has been experiencing a medical condition. The temporal characteristics of the fluorescent light, instead of intensity, can also be detected and used to determine how long the patient has been experiencing a medical condition. The temporal characteristics can be analyzed by any suitable technique including, without limitation, directly measuring the decay time of the fluorescent emissions, by phase shift techniques, by polarization anisotropy techniques, or by any other method of detecting temporal characteristics of the fluorescent light.

In still other example embodiments of the present embodiment, the returned light can include backscattered excitation light that returns from the target tissue. Such embodiments may utilize the backscattered light alone to make a determination, or the backscattered light could be used in conjunction with fluorescent light generated by the target tissue to arrive at a determination. In some embodiments of the present embodiment, a light source for providing excitation light, and a detector for detecting returned light are arranged as a confocal system. As previously discussed, such a confocal system allows one to interrogate small volumes of target tissue within a larger volume of tissue. Confocal systems allow measurements to be conducted on volumes of tissue that are below the surface of a target tissue. Also, patient specific information could also be taken into account by a system or method in an example embodiment. For instance, a patient's age, gender, and other desirable physical characteristics could also be used in various combinations, in addition to optical information, to determine how long a patient has been experiencing a medical condition. This would allow the system or method to account for age varying characteristics such as fluorescent intensity.

The excitation light source could be a laser, a LED, a fluorescent tube, an incandescent light bulb, halogen lamp, or arc lamp, or any other type of device that is capable of providing excitation light in the appropriate wavelength range. The light source could also comprise a broadband light source such as a fluorescent or incandescent light bulb. Such a broadband light source might also be paired with one or more optical filters that are designed to pass only specific wavelength bands of light. The light source could also include any other type of light source, depending on the wavelengths of interest. For instance, the excitation light source can be He—Cd or argon-ion laser, a mercury lamp, a low power white or blue LED, etc. The excitation filter can be, for example, a long or short passband filter of a suitable wavelength. The excitation filter can be selected to attenuate wavelengths that do not correspond to the excitation wavelength. The filtered light can then be directed to a dichroic reflector, such as a long-pass dichroic reflector, for redirection towards the lens.

In order to measure fluorescence and backscatter data quickly enough to calculate the ratio of fluorescence to backscatter, a spinning filter wheel, or rapid-changing monochromator may be used and located at a point in the optical light path that is in front of a photodetector. In certain example embodiments, a spinning filter wheel comprises a circular filter array that has a pattern of four filter elements or materials that allow transmission of alternating wavelengths at different rotational positions around the circular filter array. The filter array may be rotated to discrete angular positions via a motor. A system of repeatedly returning to a desired angular position can be provided by a dial or by a memory element associated with the motorizing system. Some examples of a motorizing system are a stepping motor capable of initializing the angular position, or, a servo motor with an encoder which provides initializing information. By using a spinning filter wheel, more data points can be collected and averaged to obtain a nearly real-time data collection. This can be achieved because each data measurement is taken much less than 30 seconds apart (as in the Accu-Chek D-Tector). Filter selection by continuous rotation of the filter wheel directly attached to a step motor shaft permits rapid (i.e., several cycles per second) filter changing. In particular, two pairs of blue (to measure Rayleigh backscatter) and green (to measure fluorescence) filters are located alternately around the face of the wheel. The use of 4 filters allows the use small lower cost circular filters instead of two larger custom semicircular filters. The identity of which filter is in the optical path in front of the photo detector is made by detecting encoding notches along the perimeter of the filter wheel rim with a pair of optobreakers or the like.

In operation, a first scan along the optical axis is taken within 1.5 seconds to measure the location of the front and back of the crystalline lens, followed by a second scan. During the second scan, the filter wheel is fully rotated 4 times per second (i.e., every 0.25 second) in order to accommodate 16 filter changes per second. For example, a total of 50 readings may be taken per filter every 0.25 second. As a result, a skilled artisan will appreciate that use of a spinning filter wheel is a drastic improvement over the filter sliding mechanism employed by the Accu-Chek D-Tector. In particular, collection of two sample volumes can be consistently achieved in ten (10) seconds or less, and in some cases, eight (8) or less.

Below is a schematic depicting an example embodiment of an apparatus of the embodiment comprising a confocal setup (it will be noted that unlike previous apparatuses, the light path does not encounter any beam splitters or dichroic mirrors, thereby increasing energy of the light transmission):

Alternatively, in another exemplary embodiment, the moving parts required by the presence of a spinning filter wheel, which are susceptible to periodic mechanical maintenance to prevent failure, may be eliminated via a light detection system that employs a dichroic beam splitter (or dichroic mirror) and two photodetectors, whereby light having a wavelength greater than 500 nm is reflected by the beam splitter to a first detector while light whose wavelength is less than 500 nm is transmitted through the beamsplitter to a second photodetector. This configuration has an advantage of no moving parts and there is no dead time in reading both channels because two photodetectors are collecting data 100% of the time. In a fluorescence microscope, the dichroic mirror separates the light paths. In other words, the excitation light reflects off the surface of the dichroic mirror into the photodetector. Fluorescence emission passes through the dichroic to the photodetection system. As stated above, the dichroic mirror's inherent special reflective properties allow it to separate the two wavelengths—called the transition wavelength value—which is the wavelength of 50% transmission. The dichroic mirror reflects wavelengths of light below the transition wavelength value and transmits wavelengths above this value. Ideally, the wavelength of the dichroic mirror is chosen to be between the wavelengths used for excitation and emission. However, about 90% of the light at wavelengths below the transition wavelength value are reflected and about 90% of the light at wavelengths above this value are transmitted by the dichroic mirror. When the excitation light illuminates the ocular lens, a small amount of excitation light is reflected off the optical elements within the objective and some excitation light is scattered back into the objective by the sample. Some of this excitation light is transmitted through the dichroic mirror along with the longer wavelength light emitted by the sample. This "contaminating" light can be prevented from reaching the detection system by the use of a wavelength selective element, such as an emission filter.

In an exemplary embodiment, two filters are used along with the dichroic mirror. An excitation filter may be used to select the excitation wavelength by placing the excitation filter in the excitation path just prior to the dichroic mirror. As emission filter may be used to more specifically select the emission wavelength of the light emitted from the lens of the eye and to remove traces of excitation light by placing it beneath the dichroic mirror. In this position, the filter functions to both select the emission wavelength and to eliminate any trace of the wavelengths used for excitation. These filters generally referred to as an interference filter, because of the way in which it blocks the out of band transmission. Interference filters exhibit an extremely low transmission outside of their characteristic bandpass. Thus, they are suitable for selecting the desired excitation and emission wavelengths.

Another alternative arises from the observation that the blue (scattered) signal is about 4 times the intensity of the green (fluorescence) signal. Using a 75%/25% beamsplitter with a green bandpass filter in the 25% path and a blue filter in other path will result in signals of about the same magnitude from the two detectors. A further alternative could be the use of a grating or linear variable filter wavelength dispersing element in front of a linear array photodetector. Another embodiment would be to use an electronically adjustable bandpass filter (such as a piezo controlled etalon) in front of a single photodetector. A further alternative would be to alternate between the two filters (blue and green) by moving the filters utilizing the oscillating motion of a resonant mechanical oscillator (such as a tuning fork). Still further, if only the green signal is desired, then it could be measured with a single detector and a green filter.

In an embodiment, a blue LED light source produces excitation light coupled to one or more optical bandpass filters to produce excitation light having a desired wavelength. The excitation radiation in the appropriate wavelength band is then directed through an optical delivery system which focuses the excitation light onto a target tissue in the eye of a patient. Return light, which can include a backscattered portion of the excitation light and/or fluorescent light produced in response to the excitation light, is then collected by a photo detector for analysis. One or more excitation wavelengths may be used and one or more fluorescence wavelengths may be collected.

In an example embodiment, the blue LED light source is an integrated assembly comprising a high intensity (18,000 mcd) 465 nm InGaN LED in a molded 3 mm diameter clear lensed package with a 15 degree viewing angle. This low cost, long-life light source replaces the expensive laser-based, frequency-doubled 473 nm light source in the Accu-Chek D-Tector. It will be appreciated that eliminating the laser as a light source eliminates the need for undesirable laser-safety subsystems. The integrated assembly further comprises a 1 mm diameter aperture disposed nearly in contact with the LED lens. The thickness of the aperture may be minimized to eliminate reflections from the aperture ID, e.g., via a conical shaped aperture. An optical bandpass filter may be employed to block observed spectral tails of the blue LED emission. For example, a 58 nm wide bandpass filter centered on 450 nm with 2.0 optical density blocking of out-of-band light may be employed. Further, positional adjustment of the blue LED light source assembly may be grossly adjusted laterally by movement of the mount horizontally within the limits of slotted holes for the mounting screws into the optics plate. Fine adjustment of both horizontal and vertical source position is by means of a flexure mounted structure which is adjusted and clamped by push-pull pairs of screws. It will be appreciated that additional light intensity can be obtained by using an optional LED source converging lens whereby light from the apertured LED comprises a diverging cone that overfills the source lens. The addition of a converging lens following the aperture can shrink the cone angle to just fill the source lens and thus result in more light in the source beam.

Figure 10:
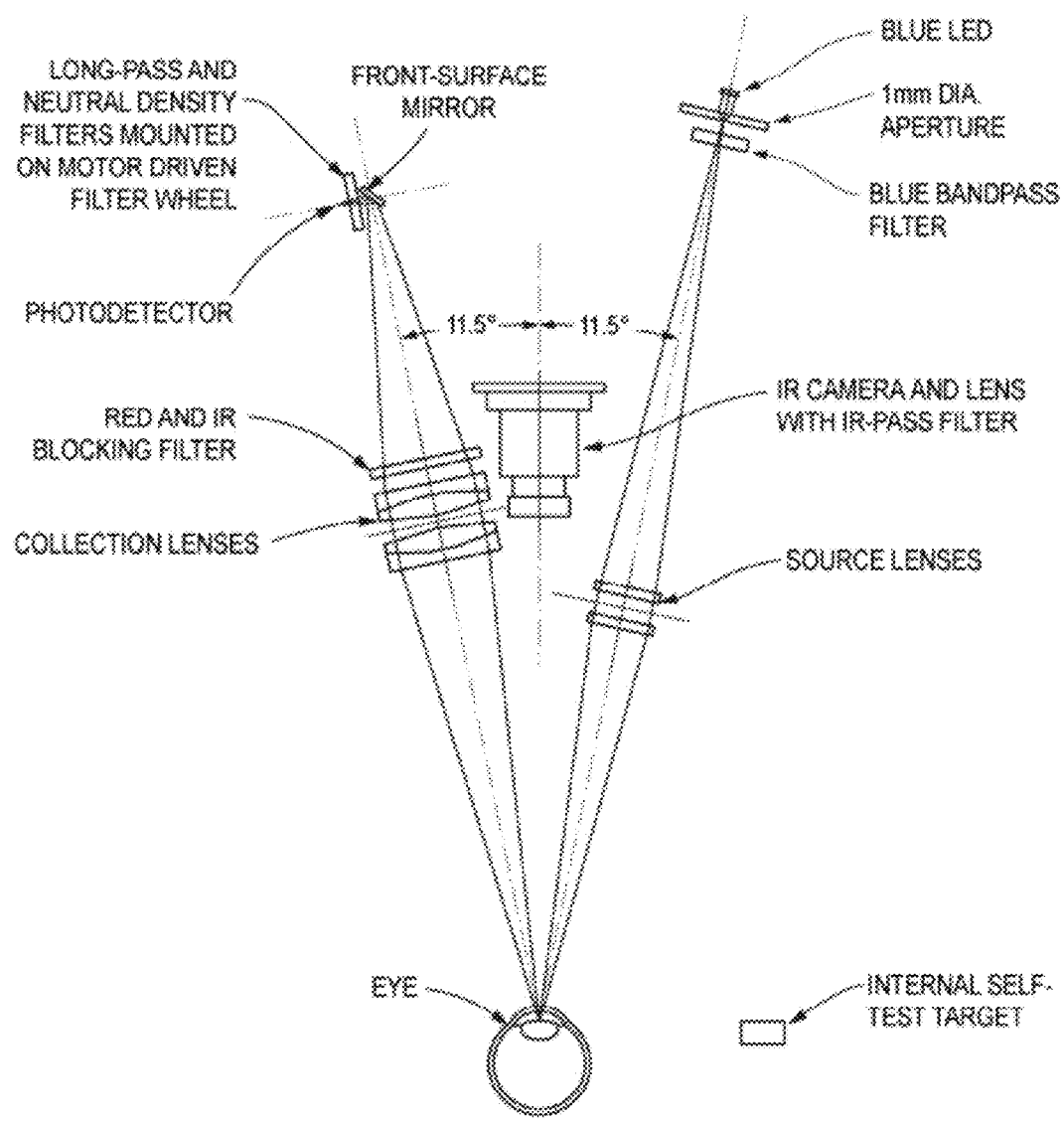
FIG. 10 depicts a schematic view of an example embodiment of an LED light optics source assembly.

In an embodiment, a blue LED light source produces excitation light coupled to one or more optical bandpass filters to produce excitation light having a desired wavelength. The excitation radiation in the appropriate wavelength band is then directed through an optical delivery system which focuses the excitation light onto a target tissue in the eye of a patient. Return light, which can include a backscattered portion of the excitation light and/or fluorescent light produced in response to the excitation light, is then collected by a photo detector for analysis. An example embodiment of an LED light optics source assembly is depicted in FIG. 10.

In the above example embodiment, the blue LED light source is an integrated assembly comprising a high intensity (18,000 mcd) 465 nm InGaN LED in a molded 3 mm diameter clear lensed package with a 15 degree viewing angle. This low cost, long-life light source replaces the expensive laser-based, frequency-doubled 473 nm light source in the Accu-Chek D-Tector. It will be appreciated that eliminating the laser as a light source eliminates the need for undesirable laser-safety subsystems. The integrated assembly further comprises a 1 mm diameter aperture disposed nearly in contact with the LED lens. The thickness of the aperture may be minimized to eliminate reflections from the aperture ID, e.g., via a conical shaped aperture. An optical bandpass filter may be employed to block observed spectral tails of the blue LED emission. For example, a 58 nm wide bandpass filter centered on 450 nm with 2.0 optical density blocking of out-of-band light may be employed. Further, positional adjustment of the blue LED light source assembly may be grossly adjusted laterally by movement of the mount horizontally within the limits of slotted holes for the mounting screws into the optics plate. Fine adjustment of both horizontal and vertical source position is by means of a flexure mounted structure which is adjusted and clamped by push-pull pairs of screws. It will be appreciated that additional light intensity can be obtained by using an optional LED source converging lens whereby light from the apertured LED comprises a diverging cone that overfills the source lens. The addition of a converging lens following the aperture can shrink the cone angle to just fill the source lens and thus result in more light in the source beam.

Using any number of suitable algorithms, pupil tracking helps to maintain alignment of the eye and to compensate for slight head or eye movements so that suitable illumination can be provided to the eye for accurate imaging/data collection. Due to the near real-time nature of the data acquisition facilitated by the use of a spinning filter wheel of the embodiment, the need for the use of a pupil-tracker and its related software/hardware to monitor movement of the eye and patient alignment during data acquisition, is virtually eliminated. Such a pupil tracking system can be implemented using any suitable imaging and/or coordinate tracking devices in the external coordinate system that can be used to track the position of a body region, e.g., patient eye. Where a patient eye is being tracked by determining the position of a geometric axis of the eye, the tracking system may include (i) a camera for imaging the body region being tracked, (ii) a light source (e.g., infrared light source) to illuminate the imaged region, and (iii) a detector on which the camera image can be represented as a digital image. A suitable tracking system may include both imaging and signal responsive elements. Standard or commercially-available imaging and image-processing system components may be adapted and employed The main body of the instrument is capable of being sealed to prevent ambient light from adversely affecting data collection by the confocal spectroscopic setup housed inside. Essentially, a patient's head is restrained by an adjustable forehead rest and chin rest. The forehead rest formed with a curvature that is smaller than that of most people's forehead to assure a stable two-point contact to the forehead at each end of the forehead rest. The forehead rest is manually adjustable in or out from the instrument to move the patient's head to accommodate the eye socket depth of the patient. A motorized chin rest is vertically movable up and down to accommodate the length of the patient's head and may be controlled by on screen buttons on the operator's computer or other suitable means. A flexible corrugated eyecup serves to block ambient light from the interior of the instrument. The eyecup is slightly compressible by the patient to assure light seal. The horizontal position of the eyecup may be adjusted by a motor controlled by an operator to accommodate patients with different interpupilary distances (PD's), thereby assuring that instrument will be horizontally positioned from the forehead/chinrest center line to correctly view the patient's eye.

The eyecup may be disposable or permanently affixed so long as it is configured to contact a patient's eye socket to substantially block out ambient light and/or to at least partially support the main body on the eye socket of the user. The eyecup has a central openings/aperture to allow passage of light from the excitation light source housed within the main body to the patient's eyes. The eyecup can be constructed of paper, cardboard, plastic, silicon, metal, rubber, latex, or a combination thereof. The eyecup can be tubular, conical, or cup-shaped flexible or semi-rigid structures with openings on either end. Other materials, shapes and designs are possible so long as ambient light is not allowed to pass through the interface between the eyecup and the patient's eye socket. In some example embodiments, the eyecup is constructed of latex rubber that conforms around eyepiece portions of the main body and is compressible (as shown). Optionally, the eyecup may be detachable from the main body after an eye scan has been completed, and a new eyecup can be attached for a new user to ensure hygiene and/or to protect against the spread of disease. The eyecup can be clear, translucent or opaque, although opaque eyecups offer the advantage of blocking ambient light for measurement in lit environments. Although the main body may comprise one or more eyecups may be orientated in a binocular fashion, only one eyecup is necessary to measure AGEs, thereby keeping manufacturing costs low. In an alternative embodiment the eyecup may be eliminated where the instrument is operated in an environment with moderate to low ambient illumination. In addition, in lieu of an eyecup, an antireflection coated window installed in the eye port prevents airflow across the patient's eye and to aid in minimizing dust accumulation on the system's internal optics. This window is tilted to avoid specular reflections back to the photodetector.

In the illustrated example, the main body is a monocular system configured to scan one eye without repositioning the oculars with respect to the head of the patient, thereby reducing the time to scan a patient. Alternatively, the main body can comprise a binocular system or dual ocular system or optical paths to both eyes for performing eye scans (for example, two oculars or optical paths for both eyes of a patient providing one view for one eye and another view for another eye, or the like), whereby both eyes are scanned simultaneously, which provides interlaces of measurements from both eyes. Other embodiments are possible as well, for example, a binocular system or a two ocular system having two respective optical paths to each respective eye can be configured to scan the eyes in series, meaning one eye first, and then the second eye. In some embodiments, serial scanning of the eyes comprises scanning a first portion of the first eye, a first portion of the second eye, a second portion of the first eye, and so on.

Other approaches are possible. In some example embodiments, for example, the main body comprises a chin rest that may be configured to automatically adjust or to allow for manual adjustment between the main body (and/or the eyecup) and the patient's eyes. The adjustment may be fine, on the order of about 0.5, 1, 2, 3, 4, 5, 10, 20, 30 or 50 millimeters. The adjustment may comprise any adjustment described herein, such as an adjustment of one or more moveable optical components to, for example, improve a field of view. In one instance, the distance between the main body and/or an optical component within the main body and the patient's eye is systematically adjusted from a first distance to a second distance. The chin rest may move in certain embodiments although in various embodiments the chin rest may be fixed and other components within the main body are movable. The distance may be based at least partly on normative values, such as an average offset (for example, in the anterior-posterior direction) between a chin and a pupil or an average distance between a pupil and an eyecup. In some instances, the distance may be determined based at least partly on a sensor reading. For example, a sensor may detect a position of the user's eye, pupil or iris. The sensor may comprise an optical or ultrasonic instrument. For example, a sensor may emit a light and determine the time elapsed between the emission and that at which reflected light (for example, a pulse) is received. The sensor may comprise a weight sensor to sense, for example, a location of the patient's chin. A sensor may detect a position or weight of the user's chin. In certain example embodiments the chin rest may move or the main body and/or eyepiece/eyecup of the main body may move with respect to the chin rest and the field of view monitored as described above to determine a suitable location of the eye. Other variations are possible.

In some embodiments, a position/setting of one or more moveable/adjustable optical components can be manually adjusted by the patient. The patient may be instructed, for example, to adjust the position/setting based on one or more images seen by the patient. For example, the patient may be instructed to adjust the position until two or more images (for example, working distance images) are aligned. Alignment may correspond to an appropriate distance of the eye to the instrument. Other designs are also possible.

Circuitry can be operatively connected to the photo detector to sample the signal strength as each of the filters within the filter wheel are aligned. The circuitry is controlled by a computer program to produce spectral data and information from the sample data. The implementation of such control and measurement circuitry is known to those skilled in the art. For instance, in an example embodiment, a computer system (not shown) is electrically coupled to an output device and a communications medium. The communications medium can enable the computer system to communicate with other remote systems. The computer system may be electrically coupled to the main body described above to collect and analyze data according to an algorithm. Alternatively, the eyecup and chin rest motors can be configured to be controlled by the computer system to semi-automatically position the eyecup and chin rest to match the inter pupillary distance between the eyes of the user/patient. In these instances, eye tracking devices may be included with a system described herein. In various embodiments, a combination of the foregoing are utilized to adjust the distance of the eyecup relative to the chin rest and/or head rest to match or substantially conform to the user's inter pupillary distance.

The inter pupillary distance may be adjusted based on the patient's viewing of a fixation targets. For example, the fixation target may be configured such that the user is required to align the fixation target with a suitable alignment means. A red LED may be used as one example embodiment of fixation targets; however, other fixation targets are possible, including but not limited to a box configuration or two or more LEDs, and the like.

Accordingly, in an example embodiment, a system as described herein may comprise software configured to determine the ophthalmic output and/or to compare measurements to other previously taken measurements (for example, measurements previously obtained from the patient or benchmark measurements). This software may be at a remote location such as a server. Raw image data or extracted numerical data may be transferred to the remote location such as the server and calculations and/or comparisons performed at that remote location. In some embodiments, data corresponding to prior tests need not be sent to the system, for example, in the case where the comparison is made at the remote location, for example, the server. In some embodiments, analysis is performed both at the location of the main body and at a remote location such as the server. Accordingly, suitable software may be included in at both the main body and the remote location. The output may include a probability, such as the probability that a condition is worsening or improving. The output may include a confidence measure. As another example, the output may indicate that an ophthalmic condition is worsening, improving or staying substantially the same. The output may comprise an appointment request. For example, if it is determined that a particular change has occurred or that a threshold has been crossed based on data obtained, output comprising an appointment request may be sent to a health care provider. The output may also comprise an indication of a recommendation for a referral or an appointment or other follow up activity.

In general, in another aspect, an example embodiment provides a system for performing at least one of light scattering and fluorescent scanning on a subject's eye, including a display screen showing an image of the eye to allow an operator to select locations in the eye to be measured. The system may include an optical unit coupled to a processor for executing scans on selected locations of the eye and for collecting data associated with the detected light scattering and/or fluorescence. The processor may further display data on the display screen for operator review. To that end, the data may be reported on the same display screen and/or collected in cycles. Moreover, the data displayed on the display screen may include test settings, front and cross-sectional views of the eye, average intensity values of detected light scattering and/or fluorescence, graphical depictions of autocorrelation functions, and curve fit parameters based on an exponential fit to the autocorrelation data. The data may be used to detect the presence of a material or object of interest, including without limitation, AGEs and/or track the progress of disease.

In some embodiments, the data collected may include the average intensity of scattered light detected and/or the average fluorescence intensity detected. Implementations of this embodiment may also collect data from locations in the nucleus and/or supranucleus regions of the lens of the eye to determine a ratio between the average fluorescence intensity associated with fluorescent ligand scanning of the nucleus region of the lens of the eye and the average fluorescence intensity of fluorescent ligand scanning of the supranucleus region of the lens of the eye. A similar ratio may be determined for quasi-elastic light scattering of the nucleus and supranucleus regions of the lens of the eye. The ratios may correlate to the state of a disease in the eye, such that an increase in a ratio indicates an increase in the amount of a material and/or object in the eye. Some embodiments may also incorporate a measurement quality metric calculated by multiplying these ratios together or using the curve, $y(t)=Le^{-kt}$, where I is the average intensity, k is the decay time constant and t is time. Additional system aspects may include a display screen for displaying the image to allow an operator to select regions of the eye for analyzing, as well as a process configured to analyze scattered light from quasi-elastic light scattering and/or fluorescent emissions from fluorescent ligand scanning to detect a material or object of interest located in selected regions of the eye. The material or object of interest may be, without limitation, AGEs. In some embodiments, the average intensity of the scattered light and/or fluorescent emissions from a supranucleus and/or nucleus region of the lens of the eye may be analyzed. Moreover, the average intensity of scattered light or fluorescent emissions from the nucleus region of the lens of the eye may be compared to the average intensity of scattered light or fluorescence for the supranucleus region of the lens of the eye to provide a correlation factor for evaluating the presence of a material or object of interest in the eye. In other example embodiments, the processor may measure the fluorescence intensity from a region of the eye before introduction of an imaging agent and after introduction of an imaging agent to determine the difference between the two intensities. In some embodiments, the processor may measure first data of fluorescence of the eye before introducing an imaging agent into the eye and second data of fluorescence of the eye after introducing the imaging agent and then compare the first data and the second data. The comparison may include, for example, subtracting the first data from the second data to determine a difference in measured fluorescence. Furthermore, the processor may display data from quasi-elastic light scattering and/or fluorescent ligand scanning on the display screen for operator review. The data may include any information on the quasi-elastic light scattering and/or fluorescent ligand scanning performed.

Still further, another exemplary embodiment is an apparatus, comprising: an excitation light source adapted to excite AGEs autofluorescence, optionally a filter to remove undesirable wavelengths and a photo detector coupled to the filter to detect an ocular tissue (e.g., retinal tissue) fluorescence signal generated in response to the excitation light and to generate a signal indicative of an integrated intensity of the ocular tissue fluorescence signal; optionally a photon intensifier coupled to the photo detector to increase the ocular tissue fluorescence signal; and a computing device communicatively coupled to the photo detector, the computing device configured to generate, based on the signal indicative of the integrated intensity, one or more of: an indication of whether a patient has diabetes (e.g., overt diabetes, pre-diabetes, gestational diabetes, etc.), an indication of whether the patient has an eye condition caused by diabetes, an indication of whether a patient has central serous retinopathy, an indication of whether the patient has diabetic retinopathy, an indication of whether the patient has retinal vascular occlusion, an indication of whether the patient has vitreoretinopathy, an indication of whether the patient has any other acquired retinopathy, an indication of whether the patient has age-related macular degeneration, an indication of whether the patient has inherited retinal degeneration, an indication of whether the patient has pseudotumor cerebri, an indication of whether the patient has glaucoma.

Advantages of the example embodiments may be realized and attained by means of the instrumentalities and combinations particularly pointed out in this written description. It is to be understood that the foregoing general description and the following detailed description are exemplary and explanatory only and are not restrictive of the claims.

While example embodiments have been described in detail, the foregoing description is in all aspects illustrative and not restrictive. It is understood that numerous other modifications and variations can be devised without departing from the scope of the example embodiment.

While the example embodiments have been described in connection with what is presently considered to be practical for intended purposes, it is to be understood that the descriptions are not to be limited to the particular disclosed embodiments, but on the contrary, is intended to cover various modifications and equivalent arrangements included within the spirit and scope of the example embodiment. Those skilled in the art will recognize, or be able to ascertain using no more than routine experimentation, many equivalents to the specific Example embodiments specifically described herein. Such equivalents are intended to be encompassed in the scope of the claims, if appended hereto or subsequently filed.

What is claimed is:

1. An apparatus for determining characteristics of biological tissue or other medium of a subject, comprising:

a) means for illuminating the medium with electromagnetic radiation directed into the medium, the means for illuminating comprising a blue LED light source, thereby causing the medium to react with a first action selected from the group consisting of reflecting, backscattering, transmitting, and emitting responsive radiation and a second action selected from the same group excluding the first action;

b) a detector for collecting the responsive radiation;

c) an optical filter connected to the detector, for separating the collected radiation into a plurality of components, wherein the plurality of components comprises a fluorescent component;

d) a processor operable to (i) measure the intensity of each of the separated plurality of components and (ii) determine a mathematical relationship between the separated plurality of components;

e) a LED fixation tube for guiding the subject to self-align itself along an axis;

f) a lens, optically responsive to the light from the light source, for focusing the light; and g) a lens system, optically responsive to the focused light, having a focus, and defining an aperture at its focus of less than approximately 1 cm, wherein the wavelength of the fluorescent component of the radiation is selected from the group consisting of between approximately 465-500 nm and 520-600 nm.

2. An apparatus according to claim 1 in which the means for illuminating causes the medium to react by emitting responsive radiation, further comprising means for measuring the time difference between illumination of the medium and emission of the responsive radiation.

3. An apparatus for measuring molecular changes in a patient having an ocular lens that, when illuminated, results in radiation including fluorescent and Rayleigh components of determinable intensities, comprising:

a) means for illuminating the ocular lens with light having a wavelength resulting in radiation in response to the illumination, the means for illuminating comprising a blue LED light source;

b) a detector responsive to the radiation, for collecting the radiation;

c) an optical filter for separating the radiation into fluorescent and Rayleigh components;

d) a processor operable to (i) detect the intensity of each of the separated fluorescent and Rayleigh components and (ii) calculate the ratio of the detected intensities, thereby producing a measurement of molecular changes in the ocular lens; and e) a LED fixation tube for guiding the subject to self-align itself along an axis;

f) a lens, optically responsive to the light from the light source, for focusing the light; and g) a lens system, optically responsive to the focused light, having a focus, and defining an aperture at its focus, wherein the wavelength of the fluorescent component of the radiation is selected from the group consisting of between approximately 465-500 nm and 520-600 nm.

4. An apparatus according to claim 3 further comprising an eyepiece means, responsive to the radiation, for permitting an operator to view the ocular lens.

5. An apparatus according to claim 4 in which the optical filter comprises at least one dichroic beam splitter.

6. An apparatus according to claim 5 in which the detector comprises at least one single chip silicon detector.

7. An apparatus according to claim 6 further comprising an amplifier.

8. An apparatus according to claim 7 in which the means for illuminating is operable to adjust the power level of the light source.

9. An apparatus for measuring molecular changes in a patient having an ocular lens having a volume that, when illuminated, results in radiation including fluorescent and Rayleigh components of determinable intensities, comprising:

a) a blue LED for providing light having a selected wavelength and power level, wherein the power level is adjustable in response to the provided light;

b) a lens, optically connected to the adjusting means, for focusing the light;

c) a first optical fiber, optically connected to the lens, for receiving the focused light;

d) a lens system, optically connected to the first optical fiber and defining an aperture having a focus greater than approximately fifteen micrometers, for delivering the focused light to selected approximately two hundred micrometers of the volume of the ocular lens, thereby resulting in radiation in response to the delivered light;

e) a collector (i) having a focal point encompassing the selected volume of the ocular lens to which the focused light is delivered and (ii) responsive to the radiation, for collecting the radiation;

f) a second optical fiber, optically connected to the collector, for receiving the collected radiation;

g) an optical filter for separating the radiation into its fluorescent and Rayleigh components;

h) a processor operable to (i) detect the intensity of each of the separated fluorescent and Rayleigh components and (ii) calculate the ratio of the detected intensities, thereby producing a measurement of molecular changes in the optical lens; and i) a LED fixation tube for guiding the patient to self-align itself along an axis, wherein the wavelength of the fluorescent component of the radiation is selected from the group consisting of between approximately 465-500 nm and 520-600 nm.

* * * * *